United States Patent
Farr et al.

(10) Patent No.: US 8,827,899 B2
(45) Date of Patent: Sep. 9, 2014

(54) DISPOSABLE ENDOSCOPIC ACCESS DEVICE AND PORTABLE DISPLAY

(75) Inventors: Ali Farr, Palo Alto, CA (US); Mina Farr, Palo Alto, CA (US); Chris Togami, San Jose, CA (US)

(73) Assignee: Vivid Medical, Inc., Palo Alto, CA (US)

(*) Notice: Subject to any disclaimer, the term of this patent is extended or adjusted under 35 U.S.C. 154(b) by 0 days.

(21) Appl. No.: 12/884,363

(22) Filed: Sep. 17, 2010

(65) Prior Publication Data

US 2011/0028790 A1 Feb. 3, 2011

Related U.S. Application Data

(63) Continuation-in-part of application No. 12/771,087, filed on Apr. 30, 2010, which is a continuation-in-part of application No. 12/759,169, filed on Apr. 13, 2010, which is a continuation-in-part of application No. 12/413,457, filed on Mar. 27, 2009, which is a continuation-in-part of application No. 12/111,107, filed on Apr. 28, 2008, now Pat. No. 8,602,971, which is a continuation-in-part of application No. 11/233,684, filed on Sep. 23, 2005, now Pat. No. 8,480,566.

(60) Provisional application No. 61/082,432, filed on Jul. 21, 2008, provisional application No. 60/612,889, filed on Sep. 24, 2004.

(51) Int. Cl.
*A61B 1/267* (2006.01)

(52) U.S. Cl.
USPC .......................................... 600/188

(58) Field of Classification Search
CPC ..... A61B 1/267; A61B 1/2673; A61B 1/2676
USPC .......................... 600/104, 109, 160, 184–200
See application file for complete search history.

(56) References Cited

U.S. PATENT DOCUMENTS 3,581,738 A * 6/1971 Moore .......................... 600/184
4,000,417 A 12/1976 Adkisson et al.

(Continued)

FOREIGN PATENT DOCUMENTS

JP H05285154 A 11/1993
JP H05337073 A 12/1993

(Continued)

OTHER PUBLICATIONS

U.S. Appl. No. 11/233,684, filed Sep. 23, 2005, Farr.

(Continued)

*Primary Examiner* — Mary Hoffman
(74) *Attorney, Agent, or Firm* — Maschoff Brennan

(57) ABSTRACT

Various embodiments for providing removable, pluggable and disposable opto-electronic modules for illumination and imaging for endoscopy or borescopy are provided for use with portable display devices. Generally, various rigid, flexible or expandable single use medical or industrial devices with an access channel, can include one or more solid state or other compact electro-optic illuminating elements located thereon. Additionally, such opto-electronic modules may include illuminating optics, imaging optics, and/or image capture devices, and airtight means for suction and delivery within the device. The illuminating elements may have different wavelengths and can be time-synchronized with an image sensor to illuminate an object for 2D and 3D imaging, or for certain diagnostic purposes.

34 Claims, 14 Drawing Sheets

(56) References Cited

U.S. PATENT DOCUMENTS

| | | | |
|---|---|---|---|
| 4,337,761 A * | 7/1982 | Upsher | 600/188 |
| 4,437,458 A * | 3/1984 | Upsher | 600/193 |
| 4,473,841 A | 9/1984 | Murakoshi et al. | |
| 4,527,553 A * | 7/1985 | Upsher | 600/188 |
| 4,869,238 A * | 9/1989 | Opie et al. | 600/109 |
| 4,901,708 A * | 2/1990 | Lee | 600/188 |
| 4,974,076 A | 11/1990 | Nakamura et al. | |
| 4,982,729 A * | 1/1991 | Wu | 600/187 |
| 5,025,778 A | 6/1991 | Silverstein et al. | |
| 5,056,163 A | 10/1991 | Chou | |
| 5,062,697 A | 11/1991 | Mitchell | |
| 5,166,787 A | 11/1992 | Irion | |
| 5,203,320 A * | 4/1993 | Augustine | 600/187 |
| 5,261,392 A * | 11/1993 | Wu | 600/188 |
| 5,285,397 A | 2/1994 | Heier et al. | |
| 5,305,121 A | 4/1994 | Moll | |
| 5,381,784 A | 1/1995 | Adair | |
| 5,475,316 A | 12/1995 | Hurley et al. | |
| 5,494,483 A | 2/1996 | Adair | |
| 5,538,497 A | 7/1996 | Hori | |
| 5,614,941 A | 3/1997 | Hines | |
| 5,643,221 A * | 7/1997 | Bullard | 604/194 |
| 5,645,519 A * | 7/1997 | Lee et al. | 600/114 |
| 5,647,840 A | 7/1997 | D'Amelio et al. | |
| 5,653,677 A | 8/1997 | Okada et al. | |
| 5,667,473 A | 9/1997 | Finn et al. | |
| 5,749,830 A | 5/1998 | Kaneko et al. | |
| 5,800,342 A * | 9/1998 | Lee et al. | 600/114 |
| 5,836,867 A | 11/1998 | Speier et al. | |
| 5,840,013 A * | 11/1998 | Lee et al. | 600/114 |
| 5,895,350 A | 4/1999 | Hori | |
| 6,066,090 A | 5/2000 | Yoon | |
| 6,106,457 A * | 8/2000 | Perkins et al. | 600/175 |
| 6,178,346 B1 | 1/2001 | Amundson et al. | |
| 6,203,493 B1 * | 3/2001 | Ben-Haim | 600/117 |
| 6,277,064 B1 | 8/2001 | Yoon | |
| 6,352,517 B1 | 3/2002 | Flock et al. | |
| 6,441,958 B1 | 8/2002 | Yeung et al. | |
| 6,461,359 B1 * | 10/2002 | Tribus et al. | 606/247 |
| 6,471,643 B1 * | 10/2002 | Henderson | 600/185 |
| 6,485,413 B1 | 11/2002 | Boppart et al. | |
| 6,525,875 B1 | 2/2003 | Lauer | |
| 6,616,603 B1 * | 9/2003 | Fontana | 600/199 |
| 6,648,816 B2 | 11/2003 | Irion et al. | |
| 6,711,283 B1 | 3/2004 | Soenksen | |
| 6,736,773 B2 | 5/2004 | Wendlandt et al. | |
| 6,762,794 B1 | 7/2004 | Ogino | |
| 6,878,109 B2 | 4/2005 | Yamaki et al. | |
| 6,916,286 B2 | 7/2005 | Kazakevich | |
| 7,029,435 B2 | 4/2006 | Nakao | |
| 7,048,685 B2 | 5/2006 | Sakiyama | |
| 7,074,182 B2 | 7/2006 | Rovegno | |
| 7,413,543 B2 * | 8/2008 | Banik et al. | 600/129 |
| 7,435,218 B2 | 10/2008 | Krattiger et al. | |
| 7,442,166 B2 | 10/2008 | Huang et al. | |
| 7,591,783 B2 | 9/2009 | Boulais et al. | |
| 7,819,877 B2 | 10/2010 | Guzman et al. | |
| 7,892,169 B2 | 2/2011 | Gono et al. | |
| 7,951,072 B2 | 5/2011 | Adams et al. | |
| 7,955,255 B2 * | 6/2011 | Boulais et al. | 600/177 |
| 8,212,858 B2 | 7/2012 | Schechterman et al. | |
| 2001/0007051 A1 | 7/2001 | Nakashima | |
| 2002/0001202 A1 | 1/2002 | Williams et al. | |
| 2002/0120181 A1 | 8/2002 | Irion | |
| 2002/0135871 A1 | 9/2002 | Vodyanoy et al. | |
| 2002/0143239 A1 | 10/2002 | Henzler | |
| 2002/0161283 A1 | 10/2002 | Sendai | |
| 2003/0023150 A1 | 1/2003 | Yokoi et al. | |
| 2004/0039242 A1 | 2/2004 | Tolkoff et al. | |
| 2004/0147806 A1 | 7/2004 | Adler | |
| 2004/0196364 A1 | 10/2004 | Takahashi | |
| 2004/0204628 A1 | 10/2004 | Rovegno | |
| 2005/0001899 A1 | 1/2005 | Banju et al. | |
| 2005/0014994 A1 | 1/2005 | Fowler et al. | |
| 2005/0024505 A1 | 2/2005 | Kawachi | |
| 2005/0038321 A1 | 2/2005 | Fujita et al. | |
| 2005/0043586 A1 | 2/2005 | Suzushima | |
| 2005/0043588 A1 | 2/2005 | Tsai | |
| 2005/0059860 A1 | 3/2005 | Matsumoto et al. | |
| 2005/0096502 A1 | 5/2005 | Khalili | |
| 2005/0154262 A1 | 7/2005 | Banik et al. | |
| 2005/0180700 A1 | 8/2005 | Farr | |
| 2005/0182297 A1 | 8/2005 | Gravenstein | |
| 2005/0222499 A1 | 10/2005 | Banik et al. | |
| 2005/0234296 A1 | 10/2005 | Saadat et al. | |
| 2005/0237605 A1 | 10/2005 | Vodyanoy et al. | |
| 2005/0240077 A1 | 10/2005 | Rovegno | |
| 2005/0272975 A1 | 12/2005 | McWeeney et al. | |
| 2006/0018017 A1 | 1/2006 | Takahashi | |
| 2006/0020171 A1 * | 1/2006 | Gilreath | 600/188 |
| 2006/0041193 A1 | 2/2006 | Wright et al. | |
| 2006/0069313 A1 | 3/2006 | Couvillon et al. | |
| 2006/0069314 A1 | 3/2006 | Farr | |
| 2006/0167531 A1 | 7/2006 | Gertner et al. | |
| 2006/0189845 A1 | 8/2006 | Maahs et al. | |
| 2006/0287582 A1 | 12/2006 | Toda | |
| 2007/0015964 A1 | 1/2007 | Eversull et al. | |
| 2007/0058249 A1 | 3/2007 | Hirose et al. | |
| 2007/0073109 A1 | 3/2007 | Irion | |
| 2007/0106117 A1 * | 5/2007 | Yokota | 600/120 |
| 2007/0106121 A1 * | 5/2007 | Yokota et al. | 600/188 |
| 2007/0106122 A1 * | 5/2007 | Yokota et al. | 600/188 |
| 2007/0167702 A1 | 7/2007 | Hasser et al. | |
| 2007/0213590 A1 | 9/2007 | Squicciarini | |
| 2007/0225561 A1 | 9/2007 | Watanabe et al. | |
| 2007/0276183 A1 | 11/2007 | Melder | |
| 2007/0292939 A1 | 12/2007 | Chen | |
| 2008/0045800 A2 | 2/2008 | Farr | |
| 2008/0051632 A1 | 2/2008 | Ito et al. | |
| 2008/0207996 A1 | 8/2008 | Tsai | |
| 2008/0208006 A1 | 8/2008 | Farr | |
| 2009/0099550 A1 | 4/2009 | Carrillo et al. | |
| 2010/0198009 A1 | 8/2010 | Farr et al. | |
| 2010/0234925 A1 | 9/2010 | Harris et al. | |
| 2010/0312059 A1 * | 12/2010 | Mcgrath | 600/188 |

FOREIGN PATENT DOCUMENTS

| | | |
|---|---|---|
| JP | 11216113 A | 8/1999 |
| JP | 2000245689 A | 9/2000 |
| JP | 2003093399 A | 4/2003 |
| WO | PCT/US2009/041118 | 4/2009 |

OTHER PUBLICATIONS

U.S. Appl. No. 12/111,107, filed Apr. 28, 2008, Farr et al.
U.S. Appl. No. 12/413,457, filed Mar. 27, 2009, Farr et al.
U.S. Appl. No. 12/759,169, filed Apr. 13, 2010, Farr et al.
U.S. Appl. No. 12/771,087, filed Apr. 30, 2010, Farr et al.
International Search Report and Written Opinion dated Oct. 30, 2009 as issued in International Application No. PCT/US2009/041118 filed Apr. 20, 2009.
U.S. Appl. No. 11/233,684, Jul. 13, 2009, Restriction Requirement.
U.S. Appl. No. 11/233,684, Nov. 12, 2009, Office Action.
U.S. Appl. No. 11/233,684, May 14, 2010, Office Action.
International Search Report dated Apr. 23, 2012 as received in application No. PCT/US2011/052039.
Written Opinion of the International Searching Authority dated Apr. 23, 2012 as received in application No. PCT/US2011/052039.
Backman, V., et al., "Polarized Light Scattering Spectroscopy for Quantitative Measurement of Epithelial Cellular Structures In Situ," IEEE Journal of Selected Topics in Quantum Electronics, vol. 5, No. 4, pp. 1019-1026 (1999).
International Search Report and Written Opinion Mailed Apr. 10, 2006 in related PCT application No. PCT-US2005-034793.
International Search Report and Written Opinion Mailed Oct. 30, 2009 in related PCT application No. PCT-US2009-041118.

* cited by examiner

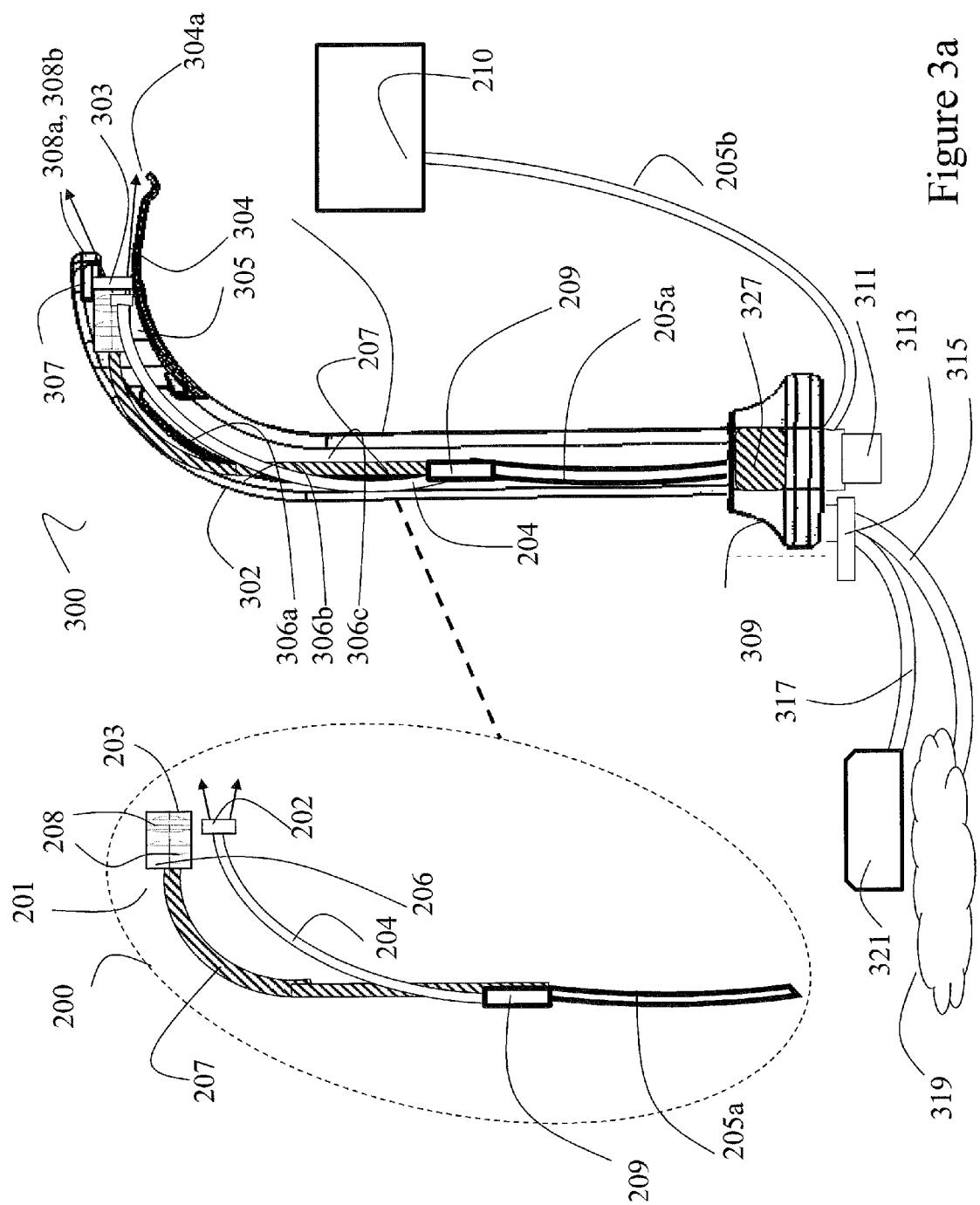

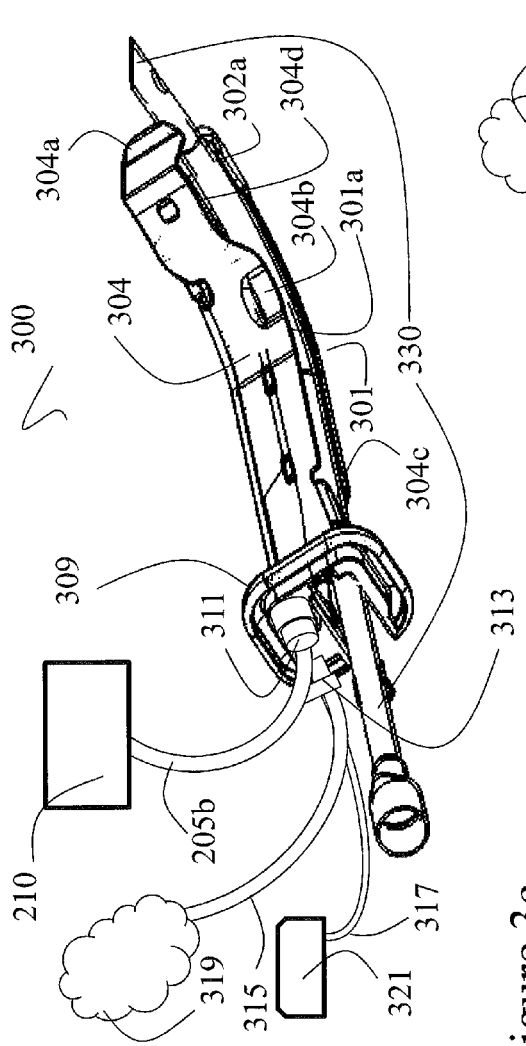
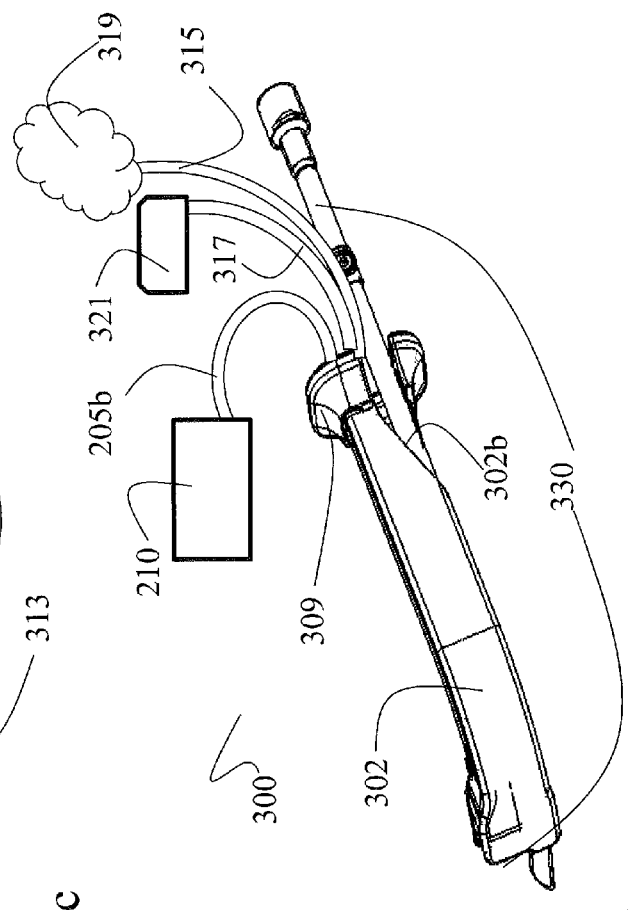
Figure 3c
Figure 3d

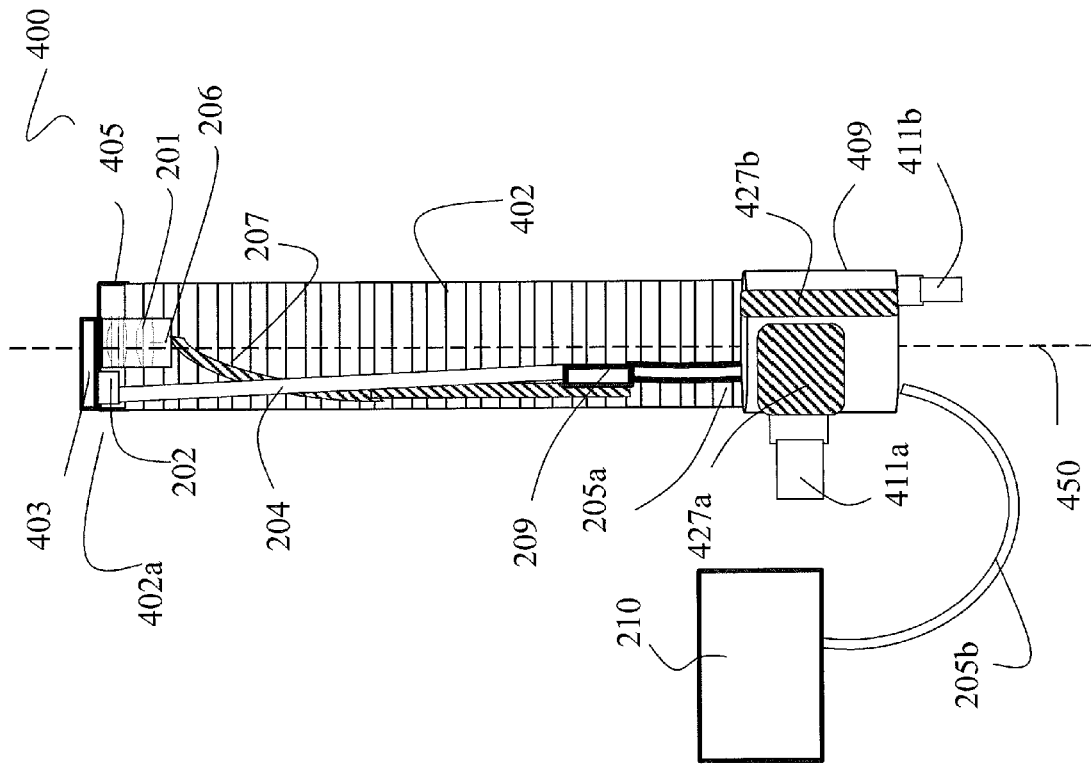
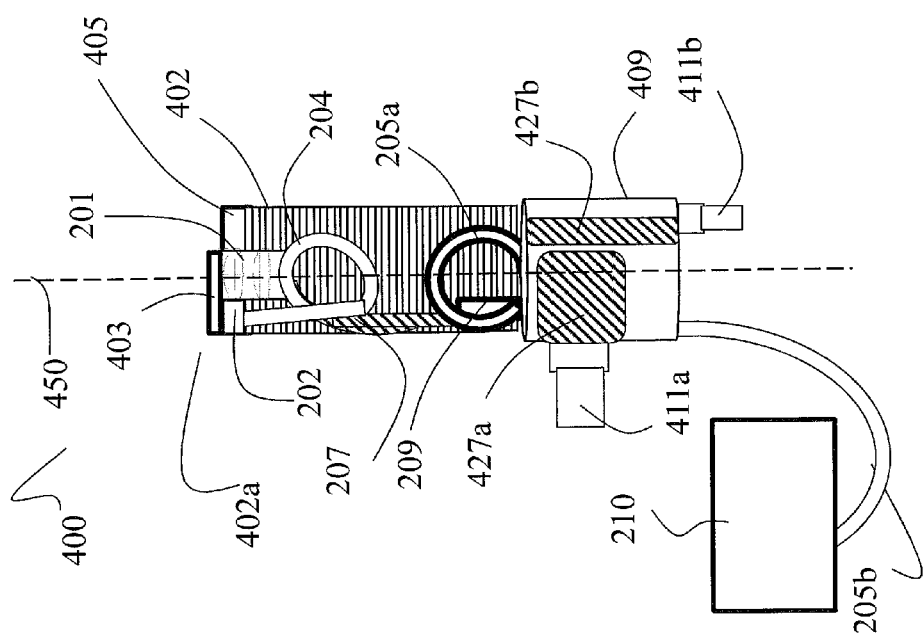
Figure 4b
Figure 4a

DISPOSABLE ENDOSCOPIC ACCESS DEVICE AND PORTABLE DISPLAY

CROSS-REFERENCE TO RELATED APPLICATIONS

This patent application:
is a continuation-in-part of U.S. patent application Ser. No. 12/771,087, filed Apr. 30, 2010 and entitled DISPOSABLE MICROSCOPE AND PORTABLE DISPLAY, which is a continuation-in-part of U.S. patent application Ser. No. 12/759,169, filed Apr. 13, 2010, and entitled DISPOSABLE ENDOSCOPE AND PORTABLE DISPLAY, which is a continuation-in-part of U.S. patent application Ser. No. 12/413,457, filed Mar. 27, 2009, and entitled PLUGGABLE VISION MODULE AND PORTABLE DISPLAY FOR ENDOSCOPY, which claims the benefit of U.S. Provisional Patent Application Ser. No. 61/082,432, filed Jul. 21, 2008 and entitled INDIVIDUAL STEREO VIEWER. U.S. patent application Ser. No. 12/413,457 is also a continuation-in-part of U.S. patent application Ser. No. 12/111,107, filed Apr. 28, 2008 and entitled OPTO-ELECTRONIC ILLUMINATION AND VISION MODULE FOR ENDOSCOPY, which is a continuation-in-part of U.S. patent application Ser. No. 11/233,684, filed Sep. 23, 2005 and entitled SOLID STATE ILLUMINATION FOR ENDOSCOPY, which claims the benefit of U.S. Provisional Patent Application Ser. No. 60/612,889, filed Sep. 24, 2004 and entitled SOLID STATE ILLUMINATION FOR ENDOSCOPY.

The above-identified patent applications are hereby incorporated herein by reference in their entirety.

BACKGROUND

1. The Field of the Invention

The present invention relates generally to an apparatus for visualization of endoscopic and borescopic fields, in minimally invasive surgical (MIS) procedures, general or diagnostic medical or industrial procedures using endoscopes or borescopes, respectively. More particularly, embodiments of the invention relate to use of portable and completely disposable endoscopic access device as a pluggable and removable vision systems in endoscopic procedures, that are completely disposable, with means of solid state illumination, image capture, equipped with an access channel, and means for suction and delivery of medication or lubricant to the endoscopic field. The device to be externally plugged into a control unit for display of endoscopic video, where the control unit provides power to the medical device, and controls and displays the visual data, through Universal Serial Bus cabling that can be disposed of along with the disposable medical access device.

2. The Relevant Technology

Endoscopy is used in both diagnostic and surgical procedures. Currently, MIS procedures, as opposed to open surgical procedures, are routinely done in almost all hospitals. Minimally invasive techniques minimize trauma to the patient by eliminating the need to make large incisions. This both reduces the risk of infection and reduces the patient's hospital stay. Endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx+the voice box), otoscope (ear), arthroscope (joint), laparoscope (abdomen), gastrointestinal endoscopes, and specialized stereo endoscopes used as laparoscopes or for endoscopic cardiac surgery.

The endoscope may be inserted through a tiny surgical incision to view joints or organs in the chest or abdominal cavity. More often, the endoscope is inserted into a natural body orifice such as the nose, mouth, anus, bladder or vagina. Laryngoscopes are used in Endo-Tracheal intubation, a common procedure performed on all patients under anesthesia and in emergency situations where a flexible plastic catheter or Endotracheal Tube (ET tube) is placed into the trachea to protect the airway and provide a means of mechanical ventilation. There are three basic types of endoscopes: rigid, semi-rigid, and flexible. The rigid endoscope comes in a variety of diameters and lengths depending on the requirements of the procedure. Typical endoscopic procedures require a large amount of equipment. The main equipment used in conjunction to the visual part of the endoscopic surgery are the endoscope body, fiber optics illumination bundles, illumination light source, light source controller, imaging camera, camera control module, and video display unit.

FIG. 1 depicts a direct laryngoscope 100 with a handle 104 containing batteries for power, and a curved Macintosh type blade 102, equipped with fiber optic or lamp illumination 106 that is used for manual direct visualization of the larynx. The Direct laryngoscope, where the practitioner obtains manual visualization of the vocal cords and tracheal opening to perform intubation, is used by anesthesiologists, on patients under anesthesia for routine airway management procedures. Where difficult airway is suspected or encountered however, more sophisticated and expensive video intubation products are used.

Due to non-portability and expensive nature of the video laryngoscope and intubation devices, most emergency intubations are also performed with direct laryngoscopy with poor success rates due to, the emergency nature of the case, unpredictability of the airway, and lack of practice by the non-anesthesiologist staff performing the procedure.

Patients that are awake during the procedure present emergency staff with more challenges, where involuntary reflexes and muscle spasms could make the tube insertion into the tracheal opening very difficult. The possibility of cuts and tissue damage to soft tissue in the mouth, throat, and vocal cord, increases with multiple attempts and forced attempts especially during emergency situations.

The cost of ownership of the video intubation devices also prohibits most hospitals in having ample equipment ready for use in all operating rooms, emergency rooms and crash carts. In emergency cases the manual visualization is at times impossible with the patient's position, circumstances that could involve other injuries such as C-Spine injury where the patient cannot be moved.

Video intubation devices currently available are also only partially disposable where a disposable cover or sheath is used to protect the reusable part of the visualization system. Various expensive visualization devices, capture electronics, rechargeable means for power, and small LCD displays mounted on the video intubation device need to be separated after use and cleaned. Improper cleaning process in these devices can lead to cross contamination and risk of infection for the patient.

Portable video intubation devices and as well as direct laryngoscopes are powered by portable batteries, within the device, where battery replacement and recharging is necessary for proper operation.

Other completely disposable intubation devices have manual visualization or allow for only a small display mounted on the intubation device itself, where shared viewing of the intubation process is not possible. In addition, most video intubation devices use analog video capture devices, where storage, transfer of the video data cannot be done without separate and secondary Analog to Digital conversion of data. Current video intubation devices are closed systems with limited process, transfer, sharing, and storage capability.

BRIEF SUMMARY

These and other limitations are overcome by embodiments of the invention which relate to a removable, pluggable, and completely disposable illumination and vision systems that can be coupled to the distal end or housed within the body of a single use removable body (access device), and subsequently attached to various other medical devices, including various functional devices used as single use disposable unit (such as ET tube in intubation procedures, biopsy tools), or autoclavable medical instruments, used in minimally invasive surgical and other diagnostic procedures. Disposable illumination and vision systems according to some embodiments of the invention include one or more solid state light sources, illumination optics (such as wave guides) and optionally include separate imaging optics and image capture devices, collectively referred to as Opto-Electronic (OE) illumination and vision modules. Removable and pluggable OE illumination and vision modules may additionally include accompanying electronics for process and transfer of the image. Moreover the complete OE vision module and electronics could be housed in a rigid, flexible, partially flexible or expandable disposable body, where the complete device including the connecting cable can be disposed of after use. Embodiments of the invention also relate to the layouts and functionality of such removable and pluggable vision systems within the body of a disposable endoscope or other disposable medical devices, or within a disposable container (access device) in which the removable and pluggable OE illumination and vision modules are housed, and plugged onto a separate non-disposable control unit. The vision system housed within a disposable access device body, can also incorporate air tight clear channels and/or flexible plastic tubing for air and liquid routing means, within the body of the disposable device as well, to enable insertion and guiding of the endo-tracheal intubation tube or other medical instruments through the access channel, as well as means to transfer gas, perform suction, deliver drug, lubricant or tissue diagnostic agents to the distal tip of the device during the procedure.

Embodiments of the invention additionally relate to general layouts of such removable, pluggable, and disposable vision systems incorporating mechanisms enabling stereoscopic, hyper or varying Field of View (FOV) visual systems.

Embodiments of the invention alternately or additionally include mobile and wearable displays that take advantage of the above embodiments. Some embodiments of mobile and wearable displays can enable minimally or non-invasive surgical and other diagnostic procedures, as well as airway management (intubation) to be performed with minimal setup needs and/or in remote locations, with full connectivity and means for recoding of procedure.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3a illustrates an example embodiment of a completely disposable anatomically shaped laryngoscope or oral access device (including blade, handle, and connecting cable) equipped with the OE vision and illumination module of FIG. 2, and with means for suction, and delivery;

FIGS. 3c-d illustrate the access channel routing and release at distal and proximal ends of the disposable endoscopic access device of FIGS. 3a-b, where the access channel is open in different sides of the device.

FIGS. 4a-d illustrate a flexible and expandable endoscopic access device similar to FIGS. 3a-e, where the device body can be deployed, and manipulated to take different shapes and forms.

FIGS. 5b-5c, illustrate 3D viewing mechanisms for the stereoscopic disposable endoscope of FIG. 5a.

DETAILED DESCRIPTION

Example embodiments of the invention are directed to completely disposable solid state opto-electronic vision modules, that can include monochromatic, polychromatic visible, Ultra Violet (UV), and/or Infra Red (IR) solid state light sources such as high power Light Emitting Devices (LEDs) and Laser Diodes as a means of illumination and one or more opto-electronic imaging systems for image capture in diagnostic, intubation or surgical endoscopic procedures or functional borescopic systems where a separate medical device (such as an ET tube) or a surgical tool can be introduced through its access channel.

In various endoscope geometries, it is also possible to install and remove the entire opto-electronic imaging system along with the LED illuminator, associated processing electronics, and cable connection for power and control of the device, within the disposable housing, from a separate power and control unit allowing implementation of a removable and pluggable opto-electronic or electro-optic (OE or EO) illumination and/or vision module, as an entirely disposable unit, of various sizes and features, as described more fully below. The removability and pluggability of such OE vision modules described herein can provide instantly upgradeable, and entirely disposable illumination and image capture systems, without any necessity to replace an entire medical or other functional control system still having a remaining useful life in a safe manner without danger of any cross contamination.

Figure 1:
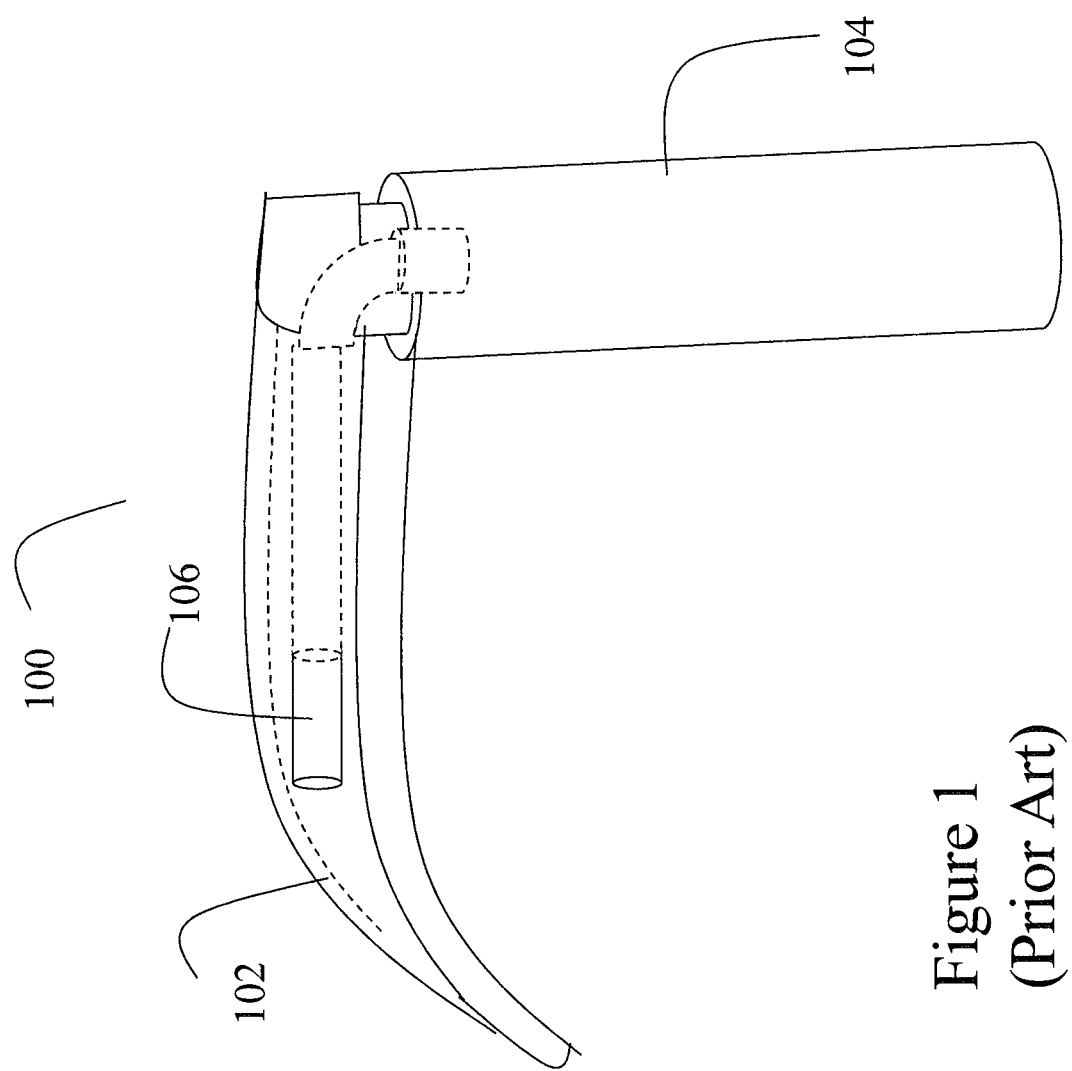
FIG. 1 illustrates a direct laryngoscope with attached Macintosh laryngoscope blade, equipped with a miniature lamp or fiber optic illumination for manual visualization of the larynx, with batteries in the handle.
Figure 2A:
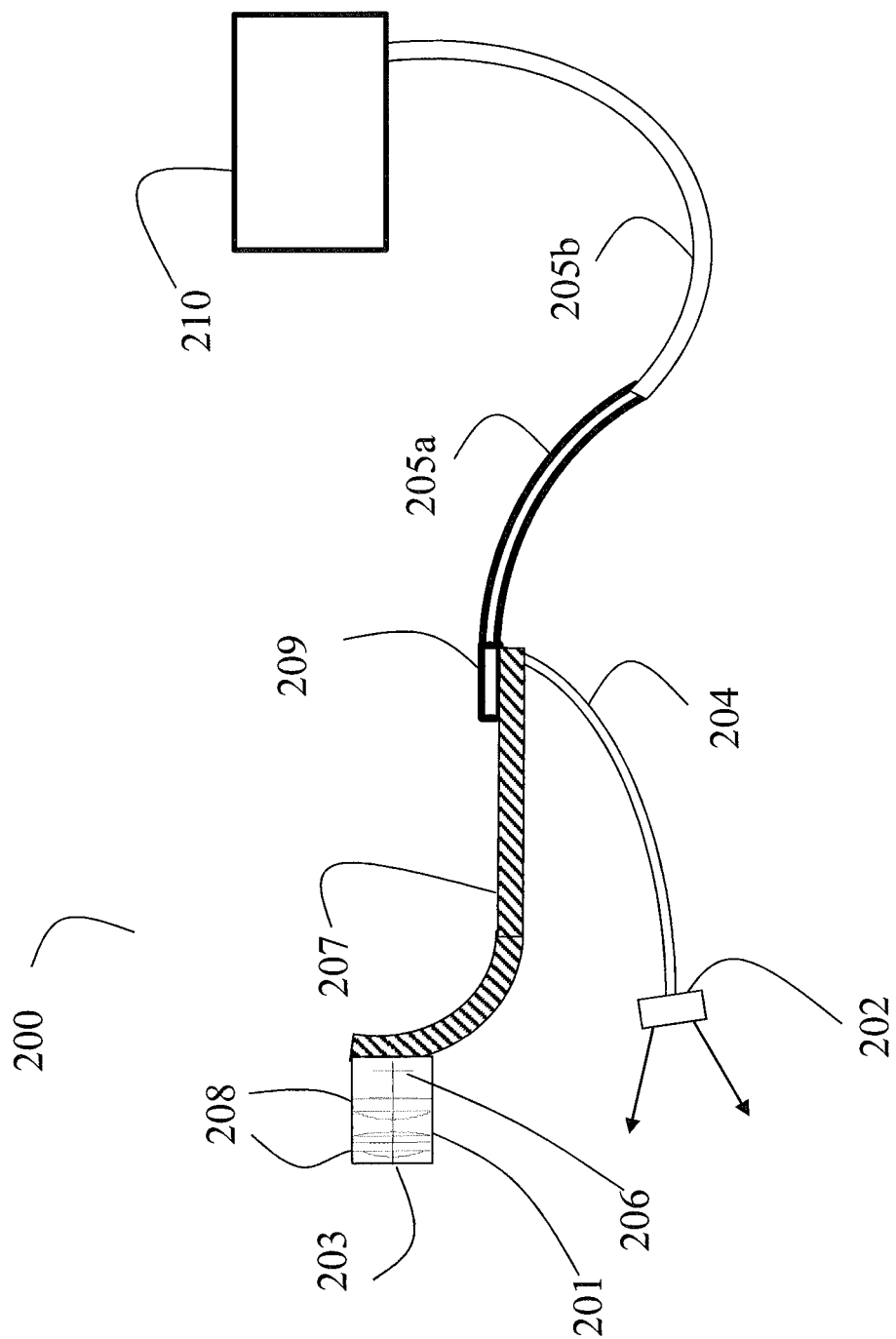
FIG. 2a illustrates a disposable LED illumination and OE vision module comprising a miniature camera unit that can be built into the distal end of a flexible or rigid medical device, and connected to a remote portable display and control unit through flexible electrical circuitry.
Figure 2B:
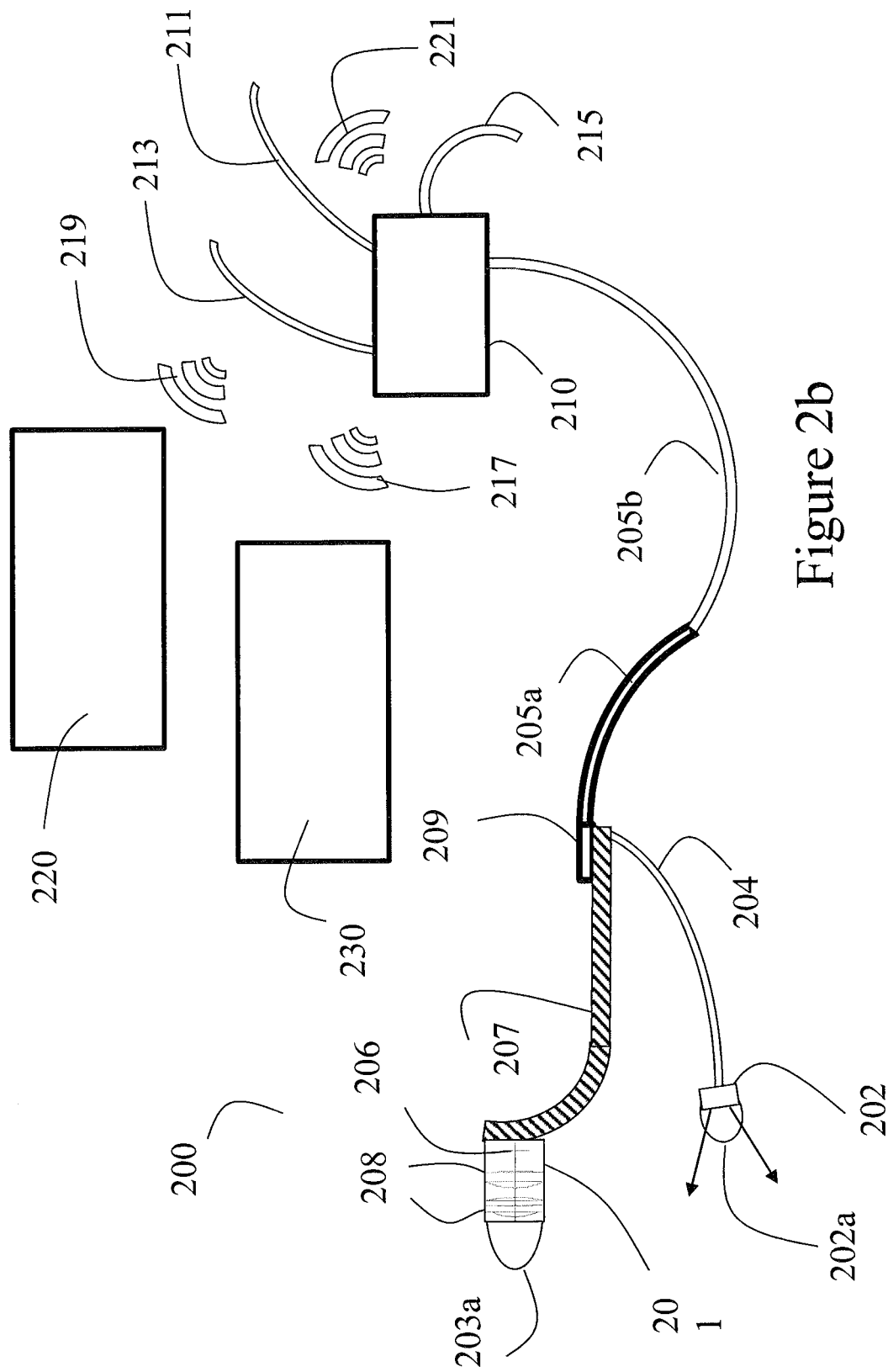
FIG. 2b illustrates the disposable LED illumination and OE vision module of FIG. 2a controlled by a multi functional control unit.

FIGS. 2a-b represent OE illumination and vision module 200, comprising a camera and housing unit 201, within which is disposed one or more imaging lenses or optical filters 208, and an image sensor 206. A clear optical window 203 (203a in FIG. 2b), is also provided to enclose the imaging lenses 208 and image sensor 206 within the camera housing of 201, that is mounted on a rigid, flexible, or combination electronic processing board 207. The pluggable OE vision module 200 can be attached to the distal end of a rigid, flexible, partially flexible, or an expandable medical device, such as an anatomically shaped, access device that is permanently shaped, pre-procedure shaped or actively manipulated during procedure, to be inserted into the body, where minimum or no force is necessary to obtain clear view of various locations inside the body. Illumination module 202 and its drive electronics can be mounted on the same electronics board 207 or have its own flexible circuitry 204, receiving power from connection 209 and electronic board 207. Flex circuitry 205a-205b can be used to provide power and control signals to the OE vision module 200 and to transmit serialized imaging signals to a portable control and display unit 210, where part of the cable (205a) can be enclosed along the flexible or rigid body of the disposable medical access device, and part of the cable (205b) can be outside the medical device, where the entire cable can be disposable along with the medical device.

The portable control and display unit 210 generally includes a display screen, housing, illumination and imaging control electronics, image processing electronics, and/or a power supply, such as a battery. Such compact vision and illumination modules 200, without means of power or control electronics of their own, can be made in a compact and low cost form to make it easily introduced into the body within a disposable housing, by itself or introduced into the body as means of access for standard medical devices, where they can be removed and disposed of after a single use. Standard low cost and proven digital electronics can be used on the flexible or rigid electronic board 207, to convert the parallel digital video signals from a high resolution digital sensor 206, for example to high speed USB (Universal Serial Bus) video class camera signals (UVC, or USB Video Class format), similar to USB Web cameras, convert and send MIPI (Mobile Industry Processor Interface) enabled serialized digital sensor outputs in UVC format directly to the Portable Display and Controller 210.

In some embodiments, flexible circuitry 205a,b communicatively couples the portable control and display unit 210 to the OE vision module(s) 201, as a USB device to communicate power and control signals, as well as serialized high speed digital video imaging signals in UVC format between the portable control and display unit 210 and the OE vision module(s) 201. As such, the flex circuitry (USB cable) 205a,b serves as one example of a means for communicatively coupling the portable control and display unit 210 to the OE vision module(s) 201. Additionally, USB cable 205a,b further communicatively couples the portable control and display unit 210 to OE illumination modules 202 to communicate power and control signals between the portable control and display unit 210 and the OE illumination modules 202. As such, the USB cable 205a,b further serves as an example of a means for communicatively coupling the portable control and display unit 210 to the OE illumination module 202 sources.

For any of the high digital speed communication methods used in USB cable 205a,b between the display and control device 210 and OE vision and illumination module 200, appropriate USB connection can be made at the display and control unit, where the entire cable 205a,b can be also disposed of, along with the OE vision and illumination module 200 that is housed in a disposable device housing. Using standard USB communication protocols and connections to the display and control unit, allows the display and control unit be or function as a computing and processing unit such as a UMPC (Ultra Mobile Personal Computer), MID (Mobile Internet Device), a Tablet Computer, or mini PC or a PDA (Personal Digital Assistant), smart cellular phone, accommodating such USB communication port. Use of such established video communication protocols such as UVC, for example in case of a high speed USB connection, makes the display and control unit to be a device readily available with multiple other connectivity solutions already available in a mobile form. As illustrated in FIG. 2b, other wired connections 211, 213, 215, could be DVI (Digital Video Interface), HDMI (High Definition Multimedia Interface), Ethernet connection, or external power adaptor connection, and wireless interfaces 217, 219, and 221 could be WiFi (wireless Ethernet), Bluetooth, UWB (Ultra Wide Band), IR, or high bandwidth cellular connection.

Other portable or non portable computing and display units, such as 220, and storage devices, such as 230, can be connected wirelessly, or with a wired connection, to the portable display and control unit 210. FIG. 2b also illustrates bulb like protective window 203a and 202a, made of thin molded plastic or glass that could be placed on the camera housing of camera module 201, and illumination module 202, to act as an optical interface and window between the camera and the illumination module where they are incorporated at the distal tip of medical devices. A single (or multiple) bulb type or flat window could act as a common (or separate) window for both the illuminator and camera in an alternate embodiment, where it can be built into the disposable medical device body, in front of the OE illumination and/or vision module 200.

Alternatively where a vision system with focusing capability is necessary, compact autofocus mechanism could be also integrated in camera module 201, where certain or all lens elements 208 are to be moved axially with respect to camera sensor 206, with drive and control signals from the control unit 210. Control unit 210 can be programmed to detect best focus of the remote camera module 201 with the imaging data it's provided from the camera and run it as if it's a local camera lens module within the control unit 201.

A fully disposable, removable and pluggable OE illumination and vision modules 200, implemented in the body of a single use disposable medical device 300 (300a with stereo vision) and 400, with an access channel 301, 401, as depicted in FIGS. 3a to 5c, can enable numerous advantages. For instance, the disposable medical device 300 (300a), and 400, housing the OE module 200, can also provide means for suction and delivery of liquid agents and medication (306a-c, 406a-b) in a fully sealed (air-tight) sterile cavity that can be disposed of after removal of the pluggable OE module 200 from the separate external power and control device 210 it is used with, whereupon a new protected OE module within a sterile device body (302, 402), can be plugged onto the power and control device 210 (and external sources of air, suction, lubrication or medication, 319 and 321) for subsequent use, thereby eliminating the likelihood of contaminating body cavities in which the disposable medical devices are used.

Some types of removable and pluggable OE vision modules 200 within the body of the a disposable device (300, 300*a*, and 400), can provide convenient access channel (301 and 401) to various designs of single use (such as various size ET tubes 330), or reusable medical devices 430 (biopsy or surgical tools) allowing for low cost variations in the medical device design and its functionality. The OE vision and illumination modules covered with a single use protective cover that is sterile (disposable device body 302, and 402) can be made in various device lengths (fixed length body 302, and variable length body 402), and provide distal tip (304*a*, 402*a*) access for various medical devices (330 and 430), where the protective cover, or the disposable body 302 and 402, with USB cable 205*a*, and possible gas and liquid tubing 306*a-c*, and 406*a-b*, running the length of the inserted disposable medical device (300, 300*a*, and 400) length, can be disposed of after use along with the entire USB cable 205*a-b*, and a new OE vision module 200 within the device 300, 300*a* or 400, and USB link can be plugged onto the medical device control system 210 for subsequent use.

Different or multiple OE vision and illumination modules 200, with various functionalities can also be plugged into the same type power and control system 210 using single or multiple USB links, directly or through USB HUBs, depending on the procedure to be performed, providing means to choose from a variety of application specific medical vision capability. For instance, white light illumination 202 or multispectral visible OE modules 200 (containing multi chip RGB LEDs in illumination module 202, that are individually controlled that can cover the visible spectrum) can be used for traditional imaging in the visible range.

A pluggable and disposable OE vision and illumination module, with additional deep blue or UV illumination 202 in device 300, 300*a* and 400 could be used to induce bio-fluorescence inside the body and detect spectral emission from the object by sensor 206, at the same time as the visible imaging, to gain further information regarding the object, such as the tissue type and identifying lesions. An IR illumination 202 can be used in the OE vision and illumination module 200, to image inside tissue or through scattering substances or fluids, to give additional in depth view. Different UV, visible and IR wavelength illumination with varying penetration depths can be used for depth dependent imaging inside the tissue. Various spectral component captured in 2D images, can be subsequently processed and put together to reconstruct a 3D view of inside the body.

LED sources in illumination module 202 can provide illumination in a wide range of the electromagnetic spectrum, from UV, to visible and IR, where the individual LED chips in 202 illuminator, each with s in a specific spectral wavelength range can be independently controlled in time by software applications running in control unit 210, and the corresponding spectral images can be independently processed based on individual sensor 206 captured frames, at the time where specific wavelength LED chip is on, by the control unit 210. Each LED spectral component can be independently designed in the LED, or obtained with independent processing of each LED spectrum, via secondary photo-luminescence process on blue or UV LEDs, or using edge or band pass spectral color filters such as multilayer dielectric optical filter coatings within illumination module 202. For imaging in the visible region, Red, Green, and Blue LED chips in primary colors can be used in illuminator 202, with or without other non-primary colors such as amber or cyan where the multiple spectral LEDs together form a white illumination, adhering to a specific color gamut set by control unit 210 by adjusting individual LED drive electronics pulsing the individual LEDs (changing the LED light intensity by adjusting the pulse width of the drive modulation).

By using multiple color LED chips in illuminator 202 and synchronizing a black and white image capture device in 206 by control unit 210, to grab the synchronized color component images, the use of color camera chips or high resolution 3 CCD or 3 CMOS imaging devices are eliminated. In this case, a single CCD or CMOS image capture device is used to capture the three or more images in a time synchronized fashion, where each color component image takes advantage of the full image capture device resolution by incorporating all the pixels in each color image component. Simple black and white image capture devices 206 are also cheaper to use, especially compared to 3 chip image capture devices, where in effect the resolution of a synchronized black and white imaging CCD or CMOS using synchronized color illumination provided by the LEDs is equivalent to a same pixel 3 chip image capture device.

Using color synchronized image capture devices 206 also allows the use of much higher resolution image capture devices in camera 201 at the distal tip 304*a*, 402*a*, of the medical access devices 300, 300*a*, and 400. A variety of illumination 202 configurations are possible using multiple LED chips in the 202 illuminator, where the uniformity, angle and extent of the illumination are freely controlled by the positioning and design of the LED chips or light source optics in illuminator 202. Various illumination fixed and deployable configurations are disclosed more fully in U.S. patent application Ser. No. 11/233,684, which has been previously incorporated by reference.

In current endoscopic imaging systems where a white light illuminator is used, the illumination spectrum is determined by the light source and the optical path the light is transmitted through before reaching the object inside the body. Subsequently, a 3-color image capture device (e.g., a single-chip RGB camera or 3-chip RGB camera) captures the reflected light from the object according to its RGB filter set and image capture device spectral sensitivity. An image display unit in turn displays the captured RGB image according to its own color filters.

Infra Red (IR), Ultraviolet (UV) LED chips, or narrow spectral band VCSELs chips can be used in illuminator 202, based on their transmission and optical characteristics in the medium of insertion, such as wavelength dependent penetration depth inside the medium or the effect they have on the object of interest (such as inducing fluorescence). By delivery and spraying of diagnostic chemical agent (using spray nozzles 308*a-b*, and 408*a-b* at the distal tip 304*a* and 402*a* of disposable medical access device 300, 300*a*, and 400, through tubing 306*a-c* and 406*a-b* from external source 321, or internal reservoirs 327, 427*a-b*), can be used to decipher cancerous cells from healthy cells in the FOV of the endoscope, when the scene under observation is illuminated by specific wavelength of light from illuminator 202, and where specific fluorescence light wavelength is detected by the OE vision module 201 sensor 206, of the device, with commands and control from unit 210. With an endoscope equipped with a full range of LED wavelengths in illuminator 202, or a specific range of illumination wavelength, it is possible to obtain a full spectral images of the object by turning the various LEDs on and off at specified times by control unit 210, and in a controlled spectral imaging range or color gamut of imaging depending on application, while a time synchronized imaging process in electronic processor in 207 in conjunction with the external control device 210, captures various spectral images based on the state of illumination 202, at the time of image capture.

FIGS. 3*a* through 3*e* illustrate a disposable video laryngoscope intubation access device 300 consisting of an anatomically shaped disposable molded plastic body 302, ending with the handle cap 309, as well as a disposable USB cable 205*a*, that is incorporated with OE illumination and vision modules 202 and 201 (depicted in dashed subset in FIG. 3*a*), and includes a power connection 209, drawing external power from the portable control and display 210 via a power line of USB cable 205*a,b*. The OE vision module 201 mounted on a rigid electrical board 207 (with flexible extension for the OE vision module), is partially connected to a distal tip component holding structure 305, with connection 209 at the opposite end of the electronic board 207, which carries power to the OE vision module 201 and illumination module 202 (see FIGS. 3*a* and 3*e*, with the LED illumination unit 202 mounted next to the vision module 201 pointing to the tip 304*a* of the laryngoscope intubation access device blade 304), and transfers serialized image data from the image sensor 206 to USB video cable 205*a*, within the body 302 of the device 300, and laryngoscope metal blade 304. USB Video cable 205*a,b* additionally provides external power from the portable control and display unit 210, which may be battery operated, to the complete video laryngoscope intubation device 300, unit consisting of the OE illumination 202 and the vision module 201.

The viewing direction of the camera module 201 can be directed and adjusted towards the tip 304*a* of the laryngoscope blade 304 by a right angle prism, mirrors, or physically locating and directing the camera unit 201, along the tip 304*a*, mounted on holding structure 305 (as depicted in FIG. 3*a*). The LED illuminator 202 could be mounted on small thermal pads or heat sink 307 directing the heat from the LED to around the edges of the front surface of imaging lens, that acts as the window 203 to the vision module for anti-fogging or alternatively to a separate imaging window 303 on the plastic device body 302, in front of the imaging optics (FIGS. 3*a* and 3*e*). Display and Control unit 210 can electronically process the video data from the vision module 201 by flipping the image or rotating it as necessary, for correct viewing of the FOV by the user with software control interface.

By incorporating the OE vision module 201 and LED illuminator 202 at the side of the distal tip 304*a* of the blade 304 (FIGS. 3*a* and 3*e*), the blade opening at distal and in proximal end, remains completely free for access to inside the body and the airway, allowing insertion of an endo-tracheal (ET) tube 330 in a straight through manner (FIG. 3*b-d*) provided by an access channel 301. Other surgical devices can also use channel 301 to gain access into the mouth and throat as well.

Figure 3B:
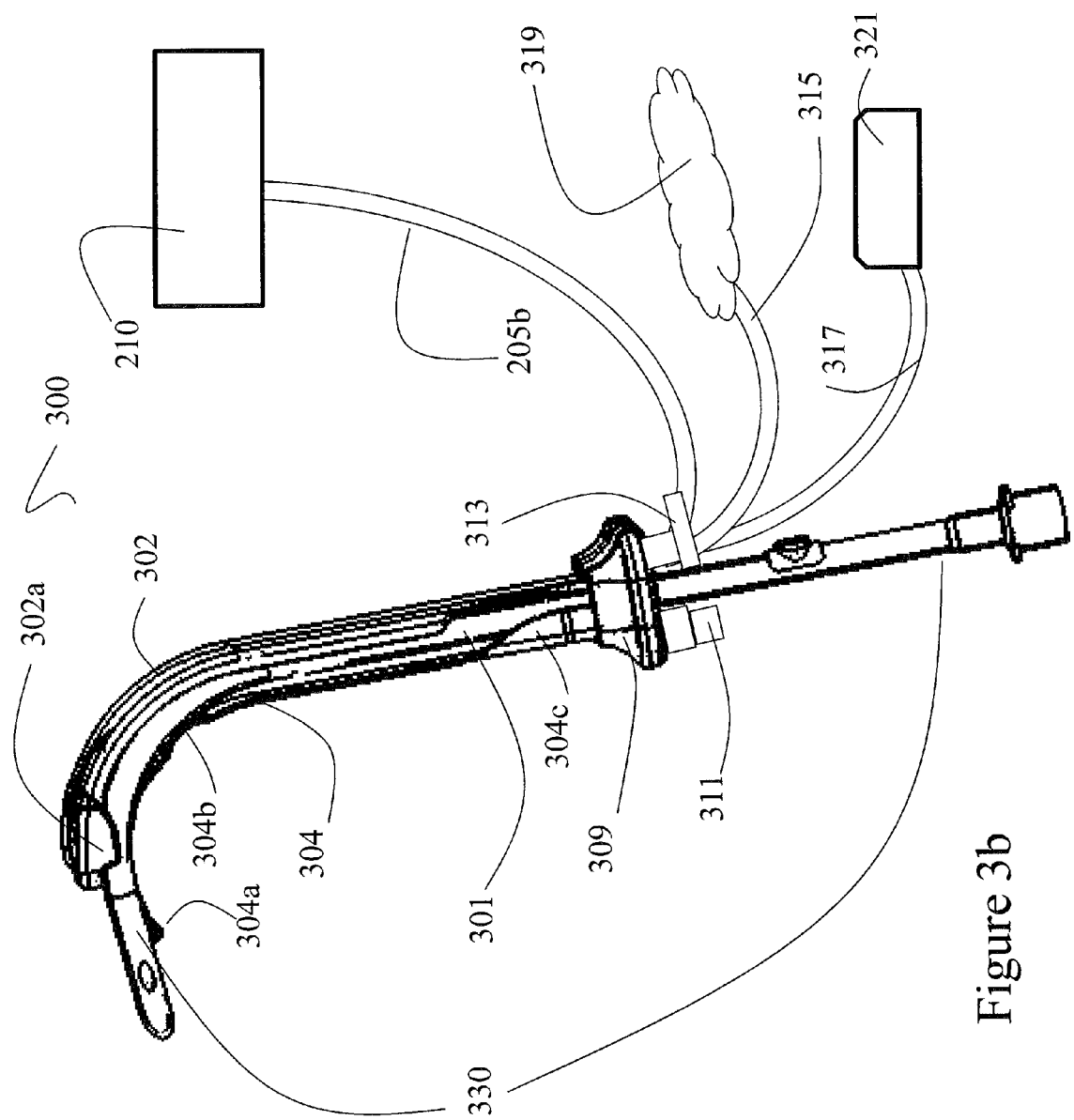
FIG. 3b illustrates the disposable oral access device of FIG. 3a, where an endo-tracheal tube is inserted into its access channel.
Figure 3E:
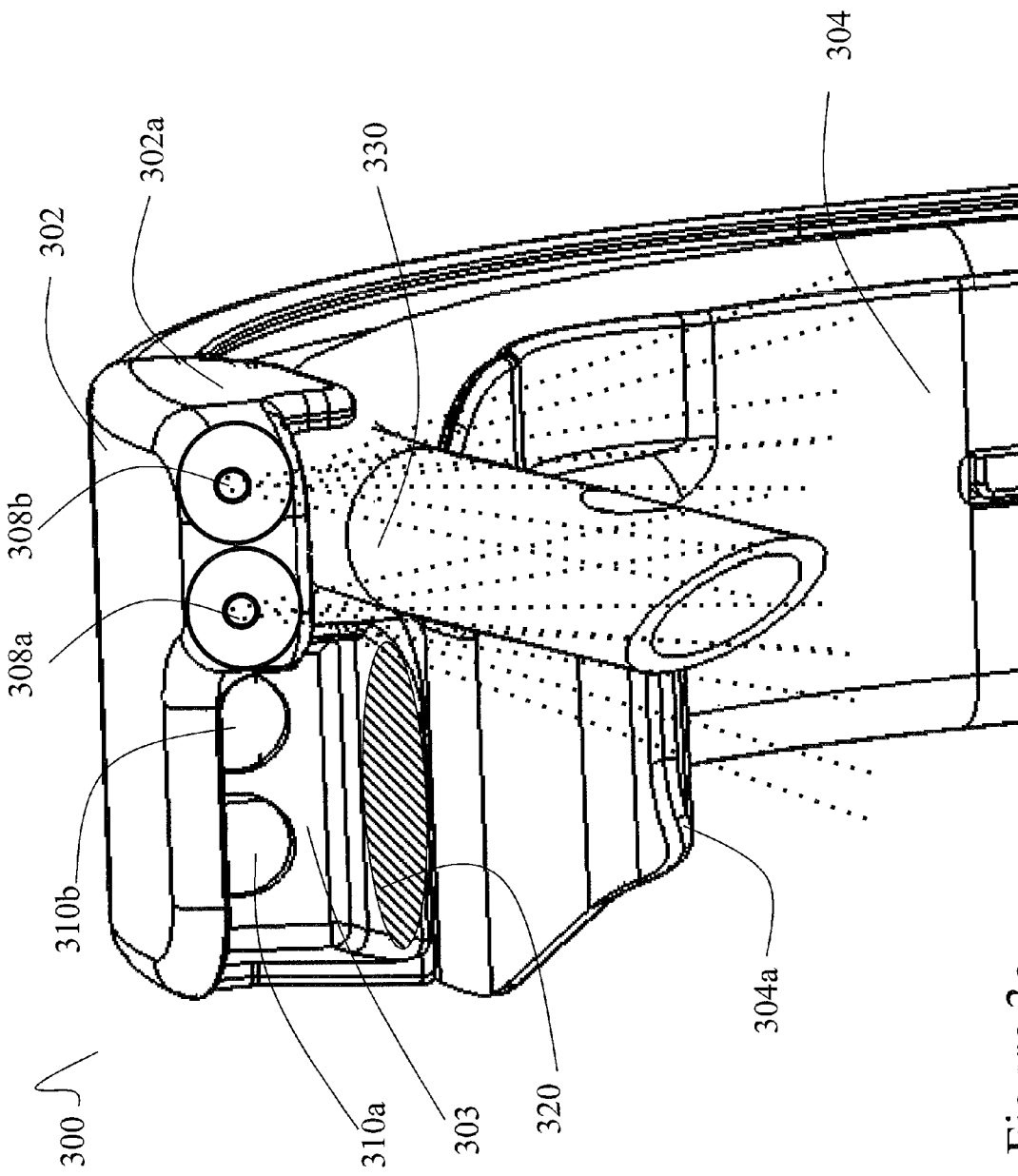
FIG. 3e illustrates a close up view of the distal tip of the device in FIGS. 3a-d, showing the OE vision and illumination ports, as well as possible suction and spray nozzles positioning.

FIGS. 3*b-d*, show an ET tube 330 inserted through access channel 301, where it is guided towards the vocal cords ahead of metal blade 304 distal tip 304*a*, by guiding features on both the device plastic body 302 such as "L" shaped tube guide 302*a*, bump 304*b* and lip 304*c*, in the metal blade 304. Access channel 301 is predominantly open on the side of the device 300 (opening 301*a*, FIG. 3*b*), however only partially open to the side at the distal tip 304*a* (partially blocked on the side by tube guide 302*a*), and blocked by handle end cap 309 at the proximal end (FIG. 3*b*). The ET tube 330 release from the access channel 301 of device is made possible at the proximal and distal tip in opposite sides of the device 300 (metal blade 304 side in FIG. 3*c*, and plastic body 302 side in FIG. 3*d*). Cut-out 302*b* in the plastic body 302 at the proximal handle end cap 309 (FIG. 3*d*) allows the tube 330 to be taken out of the access channel 301 from the plastic body 302 side, and cut-out 304*d* in the metal blade 304 allows quick release of the tube 330 at the distal tip 304*a* (FIG. 3*c*), from the metal blade 304 side and under the tube guide 302*a*. Having access channel 301 opening and release from opposing and orthogonal openings on the sides of the device (rotated openings provided by 302*b*, 301*a*, and 304*d*) at the proximal end, along the device 300 body, and distal tip, allows inserted ET tube 330 or other surgical devices to easily guided, to maintain their position and stay within the access channel 301, until exit at the distal tip and during the operation.

Device 300 of FIG. 3*a-e* is also equipped with means to perform suction at the distal tip 302*a*, and deliver liquid for irrigation, applying medication, spraying lubricants or other biomedical agents to the scene under observation, or on the surgical instruments inserted into the device 300 through access channel 301 (such as the ET tube). Since the OE vision module 200 with its electronic board 207, and electronic connection 209, is mainly located at the distal tip without taking too much room along the device body 401, various air-tight tubular channels 306*a-c*(FIG. 3*a*) or plastic tubing, can run along the plastic device body 302, next to the cable 205*a*, along the length of the access channel 301, inside the device 300, to be used for supply of suction, or means to deliver medication and biological agents to the distal tip of the device 300.

Disposable plastic tubing 315 and 317, can extend outside the medical device similar to USB cable 205*b* (FIGS. 3*a-d*), to appropriate suction chamber 319 and delivery source 321, to keep the visual field and endo-tracheal opening clear of liquids and blood, through suction opening 320 (FIG. 3*e*) close to the distal tip 304*a* and illumination and vision module ports 310*a-b*. Suction port 325 or, channels 306*a-c* can optionally contain means for filtering of air, and liquid. Small built in reservoir(s) 327 (FIG. 3*a*) with pre-filled filled liquid, medication, or lubrication gel supply can be provided at the proximal end (inside handle cap 309), and connected to plastic tubing and channels 306*a-c* inside the device body 302. A distal tip connection is made from the channels or tubing 306*a-c* to possible delivery or spraying means (openings or nozzles 308*a-b* in FIG. 3*e*) for the field in front of the distal tip 304*a* of device 300. Activation button 311 (for spraying) and valve mechanism 313 at the proximal end cap 309 (FIGS. 3*a-c*) could initiate and continue suction, spray lubricant gel on the ET tube tip as it leaves the device (FIG. 3*e*), spray antiseptics to numb the area and relax the vocal cords for easier access into the airway, cover the field of view with diagnostic agents that promote fluorescence or other chemical or visual means of tissue analysis and identifying cancerous region of the cells and tissue, through nozzles or openings 308*a-b*.

FIG. 3*e*, shows the vision module 201 and illumination 202 openings (optical ports 310*a*, 310*b*) in device 300 plastic body 302, used for vision module 201 and illuminator 202. A separate optical window 303 can be installed against these optical ports 310*a* and 310*b* in front of vision module 201 and illuminator 202 on plastic body 302 of device 300, where the heat from the illumination source is coupled to this separate window 303, to warm up the window as means for defogging.

Suction chamber 319 and delivery source 321, could be sources fixed in the medical environment that are connected to the device 300 through plastic tubing 315 and 317, or portable means to deliver these in a remote setting. In a portable setting suction chamber 319 could be a collapsed ball, bubble, bladder or container, which is made devoid of any air, where once valve 313 is released starts to expand to its expanded perform shape, initiating suction in the device 300 suction port 320. Delivery source 321 can also be a small plastic spray bottle connected the device 300 by plastic tubing 317, where when activated (press on its spray release button) initiates delivery of material to the device 300 distal tip openings or nozzles 308a and or 308b. Alternatively a syringe connection (not shown in the pictures, similar to applying medication in an IV line) can be inserted or otherwise made connection to the plastic tubing 315 and 317 junctions for on-the-go initiation of suction or delivery of medication. All means for portable suction and delivery described above are low cost portable means that could be built into the device 300 and tubes 315 and 317, where the whole mechanism and any medical and biological agents they contain can be disposed of along with the device 300 and its electrical USB cable 205a-b.

Figure 4C:
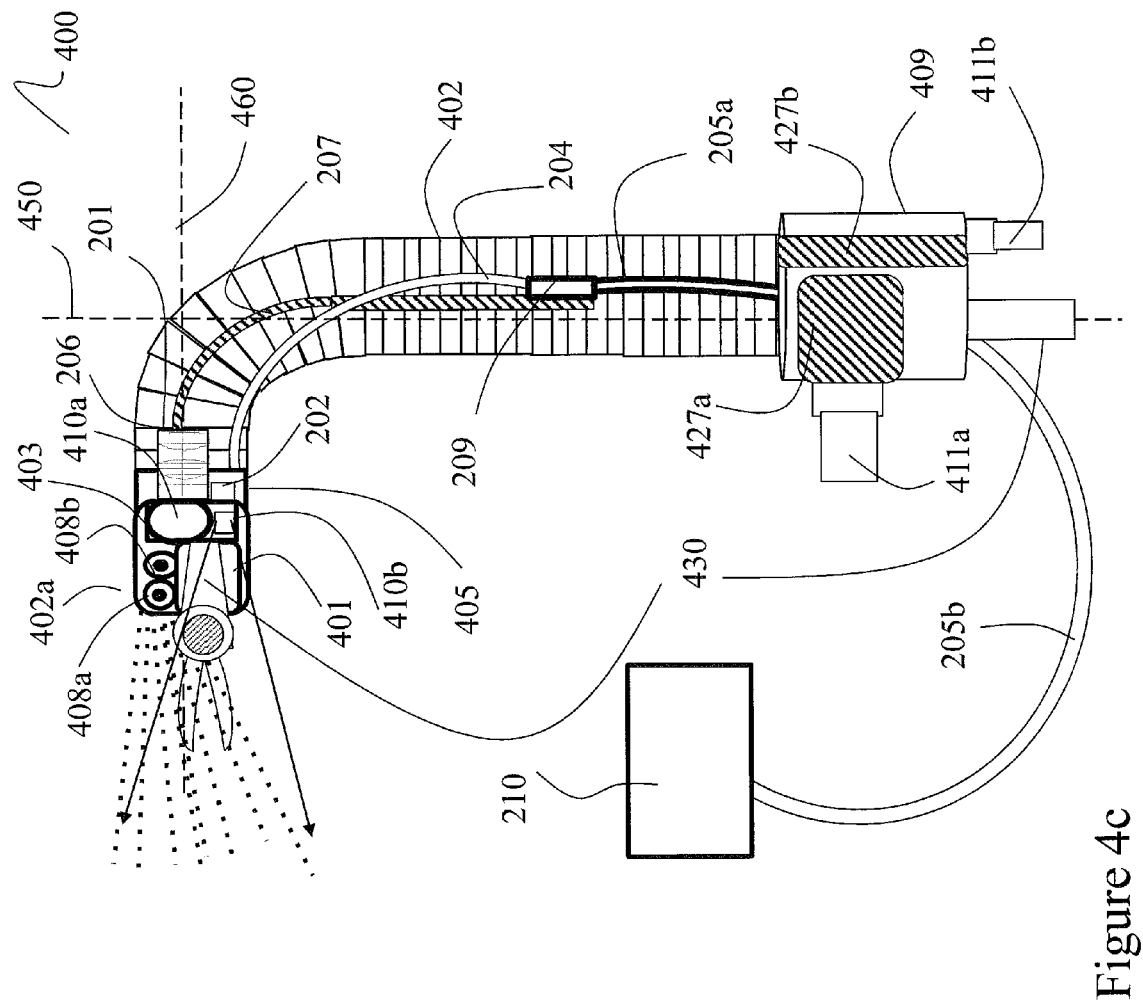
Figure 4D:
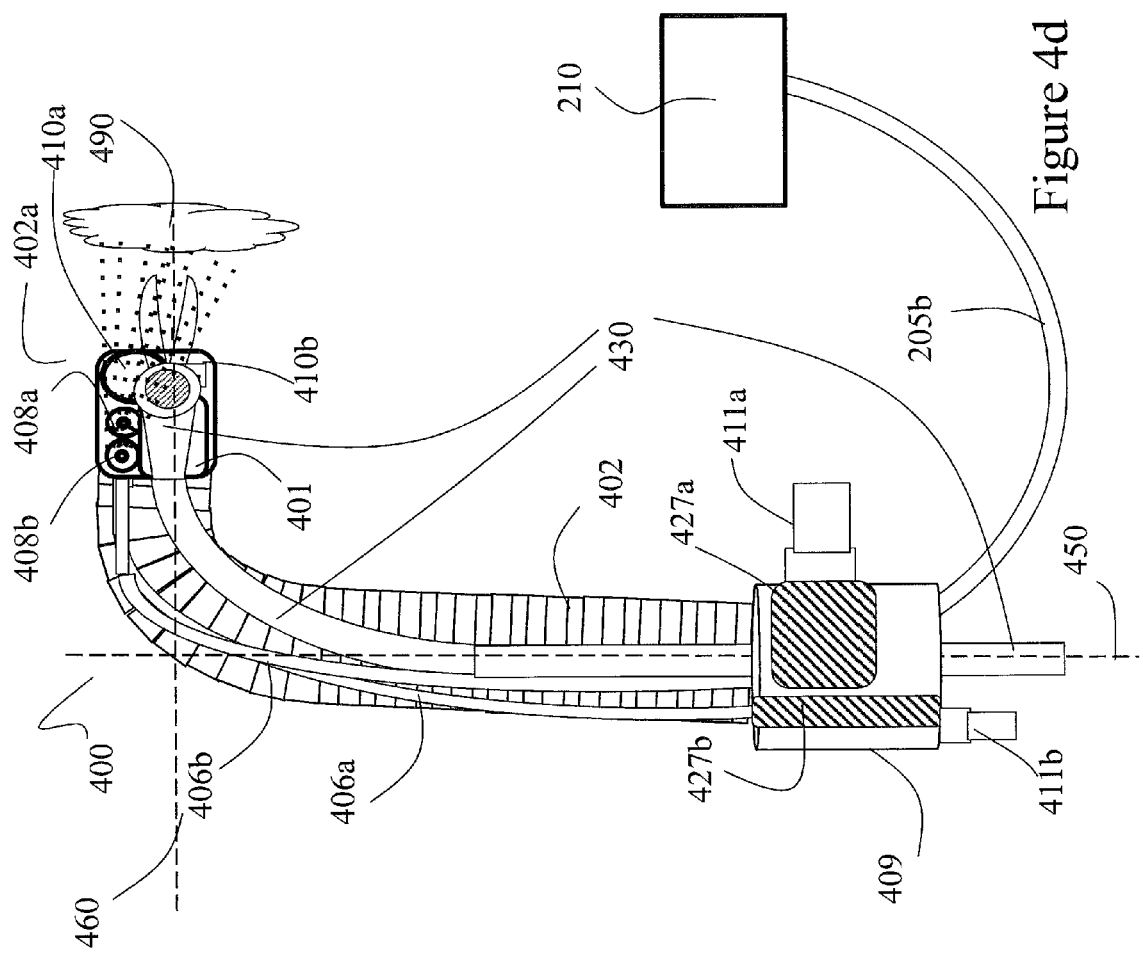

Removable and pluggable OE vision and illumination modules built into the distal tip of disposable access device (such as device 300), can also enable variety of single use disposable, articulating and non-articulating surgical medical devices (such as depicted in FIGS. 4a-d), to be used in a fixed position with respect to the medical device original form (FIG. 4a), or deployed and articulated out of the medical device body 400 (FIG. 4b-d) once the medical device distal end is inside the body. With flexible circuit connection (207 and 204) of the OE vision (201) and illumination (202) modules at the distal tip of the device 300, and flexible cabling 205a, and using flexible tubing 306a-c inside the device 300, the rigid metal blade 304 and plastic device body 302 of device 300, can be replaced with a flexible accordion type device body 402 of device 400 in FIG. 4a-d, retaining similar functionalities of device 300 but in a deployable and articulating manner. The rectangular disposable device body 402 depicted in FIGS. 4a-d, of course can have circular, elliptical of other tubular forms in a lengthwise expandable form or have shape retaining features (such as a wire) inside its tubular body 402. (as depicted in FIGS. 4a-b where accordion type body 402 is elongated along the axis 450). Through the deployment and articulation process of the OE illumination and vision modules 202 and 201 that are plugged onto the distal tip 402a of the flexible medical device 400, the OE module 200 can position itself outside the original medical device volume, creating space inside the medical device and enabling further an articulating tool's (430) insertion through the access channel 401, inside the device 400 body 402, thus allowing for further medical device functionality, or articulation to a particular position, revealing a new direction of view (460) by the medical device 400 (perhaps behind some body organs (such as the tongue, teeth, under the tongue, top of the mouth, or otherwise inside the cervix or abdominal cavity).

In the case of surgical procedures where delicate and more precise diagnostic operation or surgery is performed using the disposable endoscopic visualization access device 300 or 400, such pluggable OE vision and illumination systems 200 can not only be made in minimal size, but can alternately or additionally house two or more miniature camera systems 201 (directed towards the same FOV) with an extended dual USB device connection for stereoscopic view of the anatomy or surgical sight (as will be shown later in FIG. 5a), where and 3D viewing for extra precision and guidance with visual depth clues.

Incorporating disposable miniature solid state OE illumination and vision modules (200) in endoscope and surgical disposable access device bodies 302 (rigid) and 402 (flexible), without means for power of their own, not only eliminates device mounted displays, and large batteries used in portable devices, it also provides a highly desirable cost advantage over conventional lamp and fiber guide systems used in conventional endoscopes, as it replaces the expensive light sources, long fiber optic light guides to transfer illumination light from the light source to the scope, and the illumination light guides inside the scope as well. Low level power is needed for the LED light sources 202, image sensors 206, and drive electronics 207. The electrical connection 209 of the OE illumination and vision module 200 is also much easier using USB type communication and power protocols, with well established mobile web camera applications in video conferencing.

Only electrical power and LED control signals need to be provided for the endoscopic disposable access device 300, 300a, and 400, eliminating the heavy and bulky batteries and fiber optics illumination cable connection to the scope, increasing the maneuverability, portability and, availability, and durability of the device in a fully sterile fashion anywhere, anytime. OE illumination and vision modules 200 are also more robust to shock and vibrations, or extreme environmental conditions, and practically unlimited shelf life than fiber optic illumination, external camera systems, conventional battery, and LCD displays.

In addition to the embodiments of FIGS. 3a-e, articulating and/or deployable embodiments are possible for effective illumination and imaging of a surgical site. In articulating embodiments, such as the embodiment of FIG. 4a-c, where the OE illumination (202) and vision (201) modules are articulated from an insertion position, or deployed from a collapsed profile before use and insertion (FIG. 4a), in which they are held within a close profile of the insertion body, and along axis 450, to an operational position (FIGS. 4b-c) where they are conveniently expanded axially, deployed and articulated, pointing to an object of interest (along tip axis 460). In the original collapsed body 402 form in FIG. 4a, all flexible electronic lines and circuitry 204 and 207, flexible air and liquid tubing 406a-b(for suction, drug, diagnostic agents, etc.), are also collapsed within accordion body 402. Alternatively certain parts that are normally inside the device 400 during use, such as cable 205a (extension of USB cable 205b), or shape retaining wires inside the collapsing body 402, can be pushed outside the device from the handle 409, in the collapsed configuration of device 400 depicted in FIG. 4a. Where upon deployment, the body 402 and all the inside electrical and tubular connections are elongated (FIG. 4b), and articulated into position (FIG. 4b-c), where spray nozzles 408a-b at the end of the delivery tubes 406a-b, are also manipulated and pointed towards the same object of interest 490 (along the line of site or distal tip axis 460 in FIG. 4d). In operational position of distal tip axis along 460, the illumination light (from illuminator 202), as well as the imaging FOV (of the vision module 201), can be directed to the surgical site 490, from beyond the endoscope body 402 in FIG. 4a, where articulation of an OE module holding structure 405 at the distal end 402a, positions the vision module, and the distal tip of the access channel 401 off axis (along 460) from the axis of the insertion body (depicted by the dashed line 450 in FIG. 4a-d), increasing the functionality of the surgical device.

The portable control and display unit 210 in FIGS. 4a-c is connected to the pluggable module 200, using USB electrical cable 205b, which extends as electrical cable 205a to the electrical connection 209 of the electronic circuit board 207 of the OE vision (201) and illumination (202) module near distal end 402a of device 400 (through vision port opening 410a, and illumination port opening 410b). The vision module 201 and illuminator 202 in FIGS. 4a-c sit on a rigid component block 405 and connected to flexible section of electrical board 207, where they receive power from the electrical connection 209 (as depicted in FIGS. 4a-c), which could be made to run as a USB device. LED illuminator 202 is mounted on or near or behind optical window 403 (in front of the vision module 201), for efficient heat transfer from the LED to the window as anti-fogging means. Alternatively a passive resistor could be mounted on the window 403 to act as de-fogging unit, when the device is used inside the body with higher temperature than outside.

Multiple color LED chips can be used within the plastic tip housing 402 of the disposable device 400, where the display and control unit 210 synchronizes the on/off timing of each color LED with the frame rates of a black and white camera sensor 206. Such disposable endoscope could be used for spectral imaging with narrow band LED light output in the illuminator module, or with wider wavelength band illumination in the visible range time synchronized with a black and white image sensor 206, to provide full color vision where each color frame takes advantage of the full resolution of the image sensor 206.

In alternate embodiments of all of the pluggable OE illumination and vision modules 200 in the form of disposable, rigid or flexible access device that use LEDs for illumination, Solid State Laser Diodes (LD) or VSCELs can alternately or additionally be employed within the OE illumination and vision module or independently at the distal end of pluggable single use devices. For instance, Infrared (IR) Imaging employs IR solid state light sources to illuminate close tissue diagnostic and surgical procedures. IR detectors and special image sensors with modified optical filters or polarizers in front of their pixels can be employed within OE vision modules 200 for through tissue and blood imaging along with infrared light sources that have appreciable penetration depth in human tissue, blood or other bodily fluids, such as urine.

With use of various wavelength LED chips (UV, visible spectra, or IR) in illuminator 202, spectral imaging can be performed concurrently or at various time windows, and with spraying of the site with specific diagnostic agents using spray nozzles 408a-b (FIGS. 4c-d), under specific illumination wavelength from illuminator 202, tissue diagnosis relating the bio-fluorescence characteristics of the cells can also be performed on the area under observation (490). As in device 300, the surgical area 490 under observation of device 400, can further be locally anesthetized or numbed with medication sprayed onto the site 490, from nozzles 408a-b, were then surgical tools (430 in FIG. 4c-d), biopsy needles, or blood coagulating devices, and other tools can be inserted and used through channel 401. Spray buttons 411a and 411b installed on handle 409 and the proximal end of the disposable device 400, can activate spray of the material contained in in reservoir 427a and 427b (also enclosed inside the handle 409), through flexible tubing 406a-b, at the spray nozzles 408a-b.

Figure 5A:
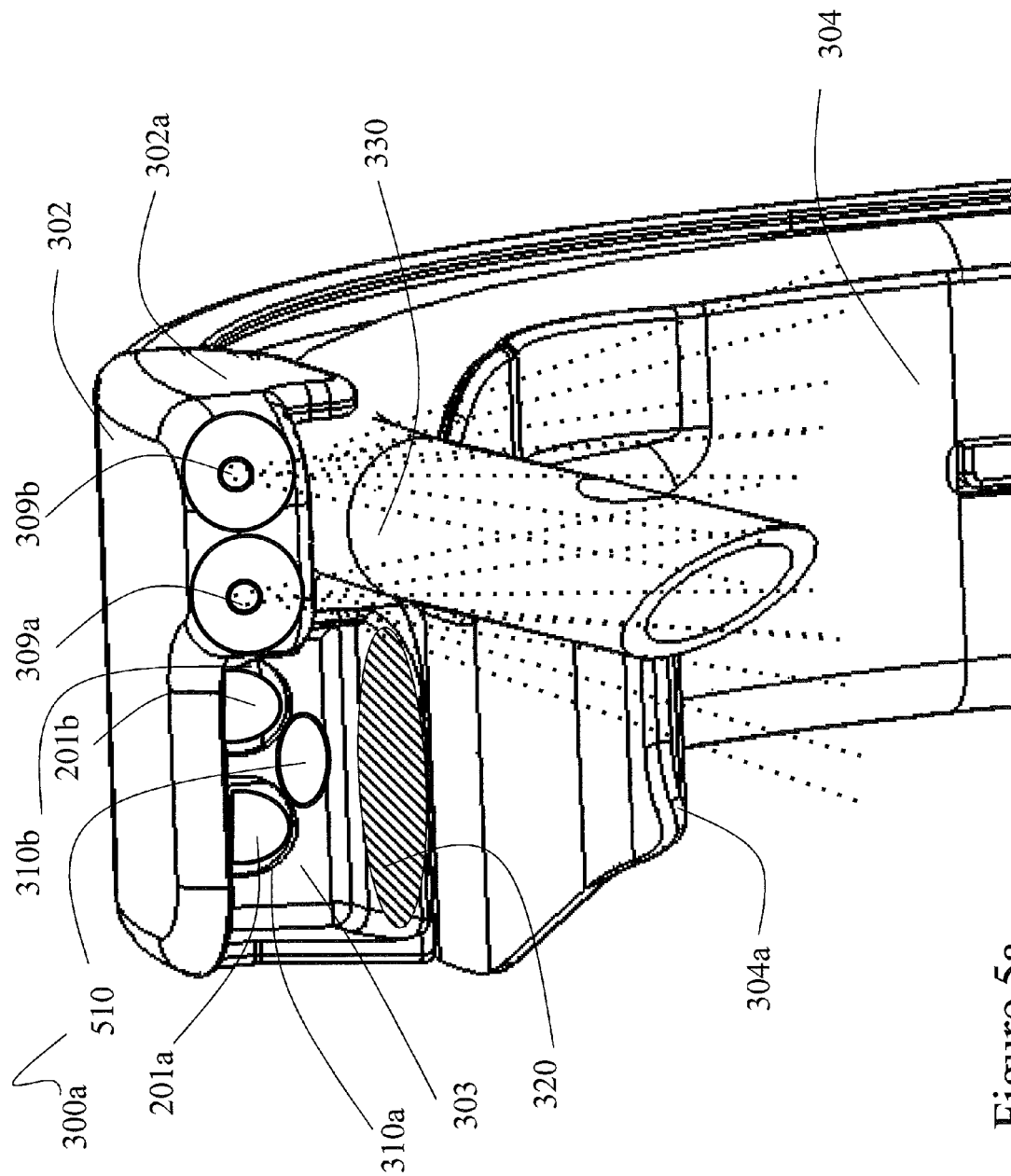
FIG. 5a illustrates a dual camera version of OE illumination and vision module of FIG. 2a, housed in the pluggable and disposable access device of FIGS. 3a-e, providing stereoscopic vision endoscopic access device.
Figure 5B:
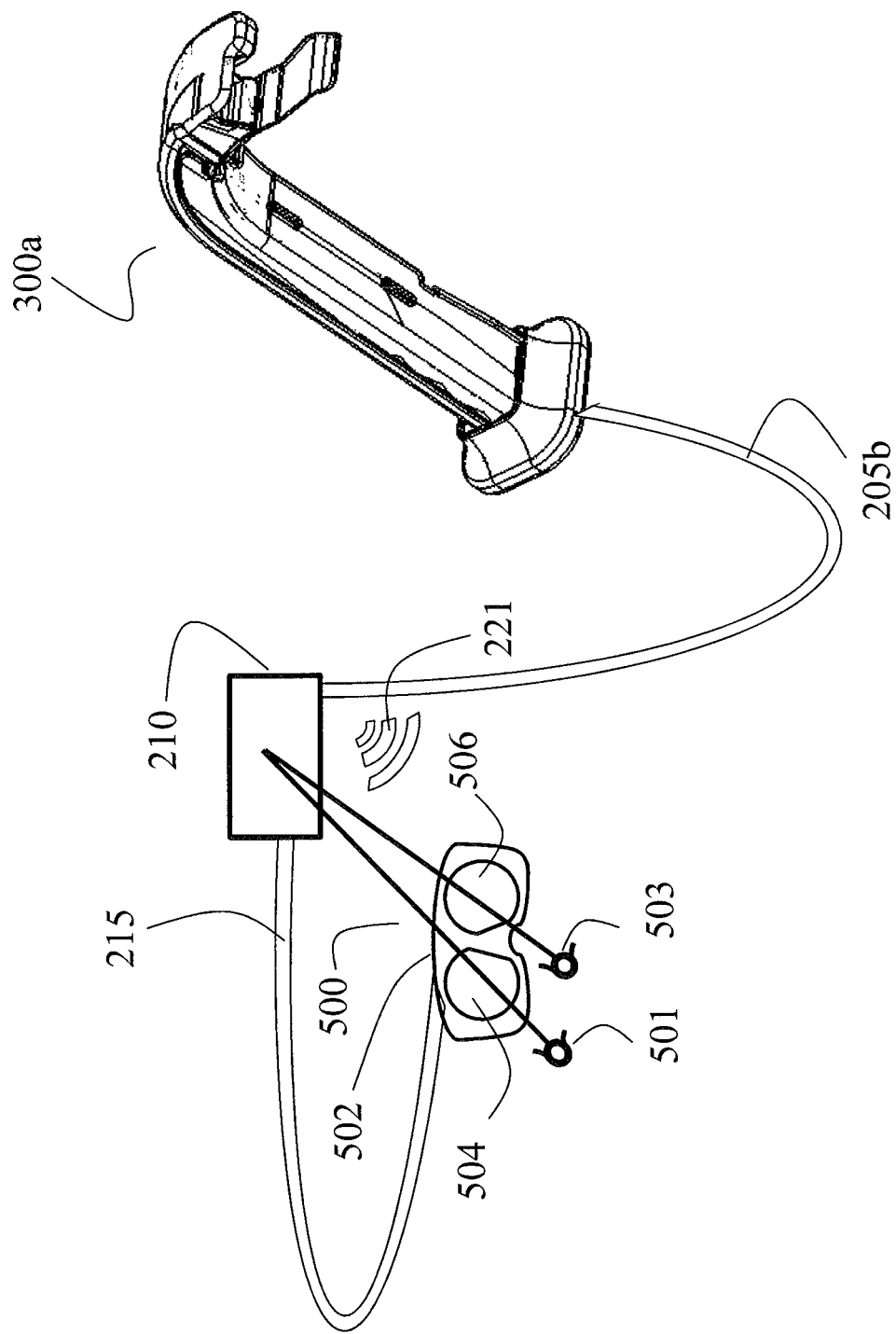

In some embodiments of the invention, multiple OE vision modules 201 are employed within a single pluggable module to obtain stereoscopic viewing in a disposable stereoscopic access device 300 or 400, as illustrated in FIG. 5a (device 300a). In these and other embodiments, the portable control and display unit 210 can be used to house all the control electronics and software necessary to power the OE vision modules 201a and 201b, (used as right and left vision modules, now mounted behind vision ports 310a and 310b of device 300 in FIG. 3e), control illumination 202 now mounted behind a new third device vision port 510, imaging functionality of illumination module(s) 200, data transmission control (using standard network device protocol such as a in a USB host driving one or more web cameras with on board illumination), as well as any image processing and/or display functionalities. For instance, the portable control and display unit 210 can include illumination and imaging control electronics that provide illumination and/or imaging control of multiple LED sources (individually, concurrently or in time) in OE illumination module 202 and/or the OE vision modules 201a,b. Alternately or additionally, the portable control and display unit 210 can include image processing electronics that provide image processing of image data received from multiple OE vision modules 201a,b, perform autofocus, or initiate drug and chemical agent delivery to the site from spray nozzles 308a-b.

The portable control and display unit 210 can be a portable display unit used in a fixed position in a medical facility, or as a mobile application with an LCD, a touch screen, or other display unit capable of displaying 2D or 3D (stereoscopic) images. The portable control and display unit 210 can alternately or additionally be worn by a user, with a wired or wireless connection to the input devices (e.g., the OE vision module(s) 200), where the user can observe 2D or 3D stereo images and video conveniently by looking at the display mounted on an arm of the user, hanging from a neck of the user, or otherwise mounted (clipped on) to the user or patient.

The portable control and display unit 210 can be electrically powered using a power cable, or use rechargeable or disposable batteries. In all the embodiments, the electrical power supply of the portable control and display unit 210, whether from a power cable or battery, provides power for the portable control and display unit 210 as well as the OE illumination and vision modules 202, 201 to which the portable control and display unit 210 is attached via USB cable 205a,b. Single or multiple OE illumination 202 and vision modules 201 can be connected to the portable control and display unit 210 (using USB HUB like connections), which portable control and display unit 210 can be configured to provide synchronized control of complete illumination and image capture for all connected OE illumination and vision module units it's connected to. The portable control and display unit 210 could also provide means for local and transferable means of image and video storage, with magnetic and/or electrical storage devices within its housing. A user interface can be provided on the portable control and display unit 210 and may include hard or soft electronic keys, a mouse or joystick, a touch screen, and/or voice activated command electronics. The user interface can be employed to adjust, control, display, process, transfer, store or retrieve the image and video data. The portable control and display unit 210 can alternately or additionally comprise a multifunctional unit that is used as both a general portable medical display and one or more of: a cell phone, a mini computer with wireless capabilities, mobile internet device (MID), a GPS unit, a personal digital assistant (PDA), a note-taking device, a dictation device, a video conferencing device, or the like.

The user interface devices described above, including hard or soft electronic keys, a mouse or joystick, a touch screen, and voice activated command electronics all serve as examples of input and/or output means that can be included in the portable control and display unit 210. The portable control and display unit 210 can alternately or additionally include computing means, such as a processor, microprocessor, controller, or the like. Alternately or additionally, the portable control and display unit 210 can include cellular communication capabilities and/or wireless connectivity.

In some embodiments that include stereoscopic or 3D image capture (device 300a, as illustrated in FIG. 5a), the portable control and display unit 210 can display time-synchronized alternate left and right frames of the video from the medical device vision modules 201a and 201b in FIG. 5a, where a pair of time-synchronized liquid crystal shutters, 504 and 506, in front of the user's left and right eyes (501 and 503), allow each eye to see the corresponding alternating stereoscopic images. In such embodiments, the user can wear 3D-viewing time-synchronized shutter glasses 500, with frame 502 depicted in FIG. 5b, while viewing the 3D displayed data on the portable control and display unit 210, and while the 3D-viewing liquid crystal shutter glasses are time-synchronized with the portable control and display unit 210 via a timing signal received via wireless interface 221 (e.g., IR connection, Bluetooth) or hardwired connection 215, to the portable control and display unit 210 as described also in FIG. 2b.

Figure 5C:
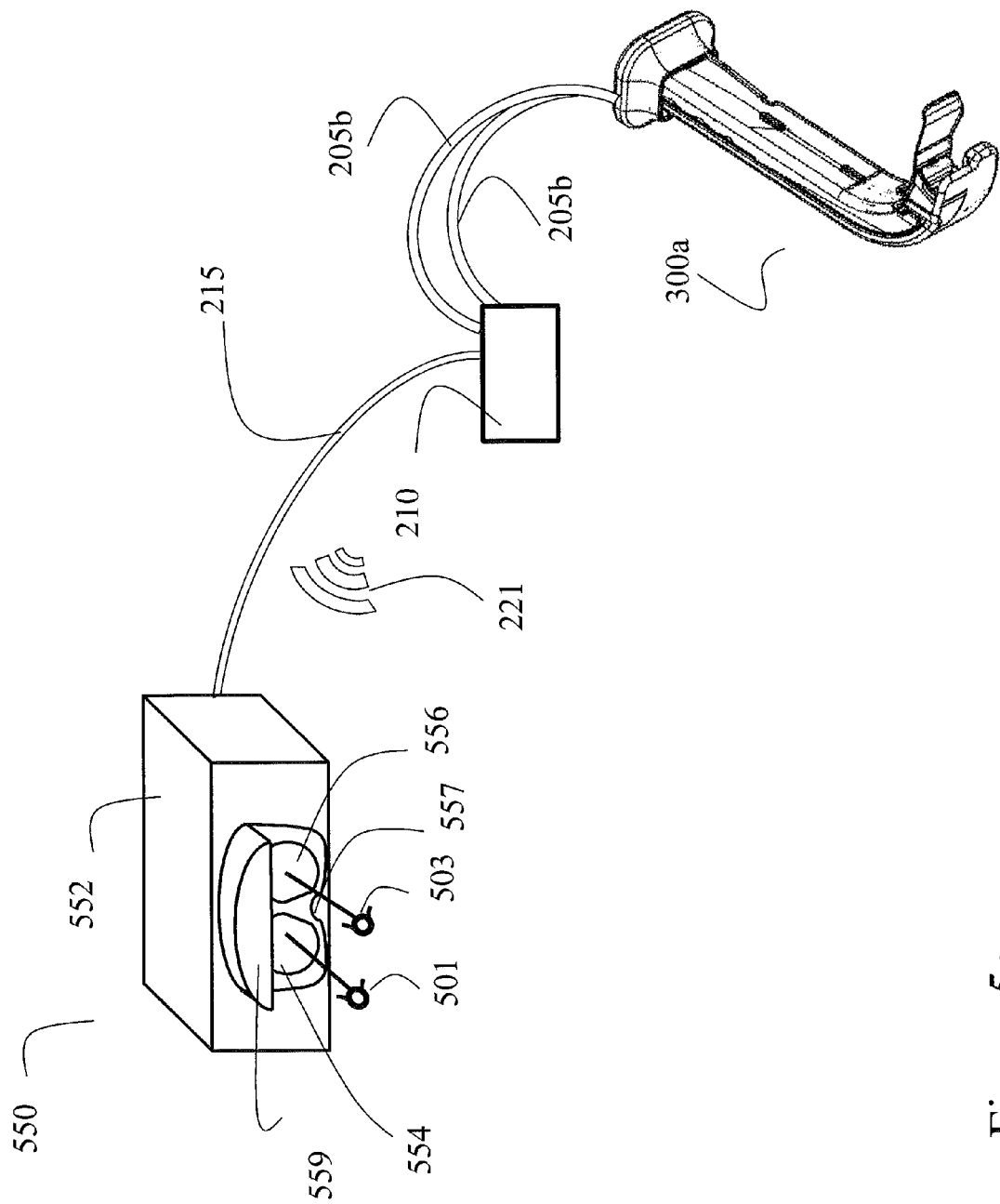

An independent 3D viewer illustrated in FIG. 5c with its' own left and right LCDs for stereoscopic viewing (or time synchronized left and right image on single LCD, similar to the display unit 210 in FIG. 5a, with left and right liquid crystal shutters 554 and 556) could be used alternatively to view the 3D video from the disposable stereo endoscope 300a (here connected using separate USB cables 205b for the left and right video). In which case the control and display unit 210 could be displaying the 2D images from either left of right vision modules 201a or 201b, while relaying the 3D video data to the 3D viewer 550 through wired or wireless connections 221 and 215. The independent 3D viewer could be equipped with headrest 559 and nose relief 557 on its housing 552.

The portable control and display unit 210 may comprise a flat panel LCD screen, touch screen, or other suitable screen such as organic LED display, or 3D LCD that can display 3D stereoscopic images with or without special (polarized) glasses. A separate sterile disposable cover could be draping the portable control and display unit, preserving all user interface and electrical connection functionalities. Alternately or additionally, the portable control and display unit 210, or it's separate sterile cover can have multiple positioning and attachment possibilities, depending on its size, the type of medical device it's used with, the type of medical procedure, the location the procedure is performed, and the type of user interface necessary. In fixed office or surgical environments, the portable control and display unit 210 can be fixed to a wall, mounted on an IV post, clipped onto as patient cover or drape, or can be hung from a frame structure, with tilt, rotation, and locking capabilities and in a removable and portable form. Alternately or additionally, a fixed control and display unit can be employed to control OE illumination and vision modules 202 and 201 and/or to display image data captured by OE vision modules 200.

Figure 6:
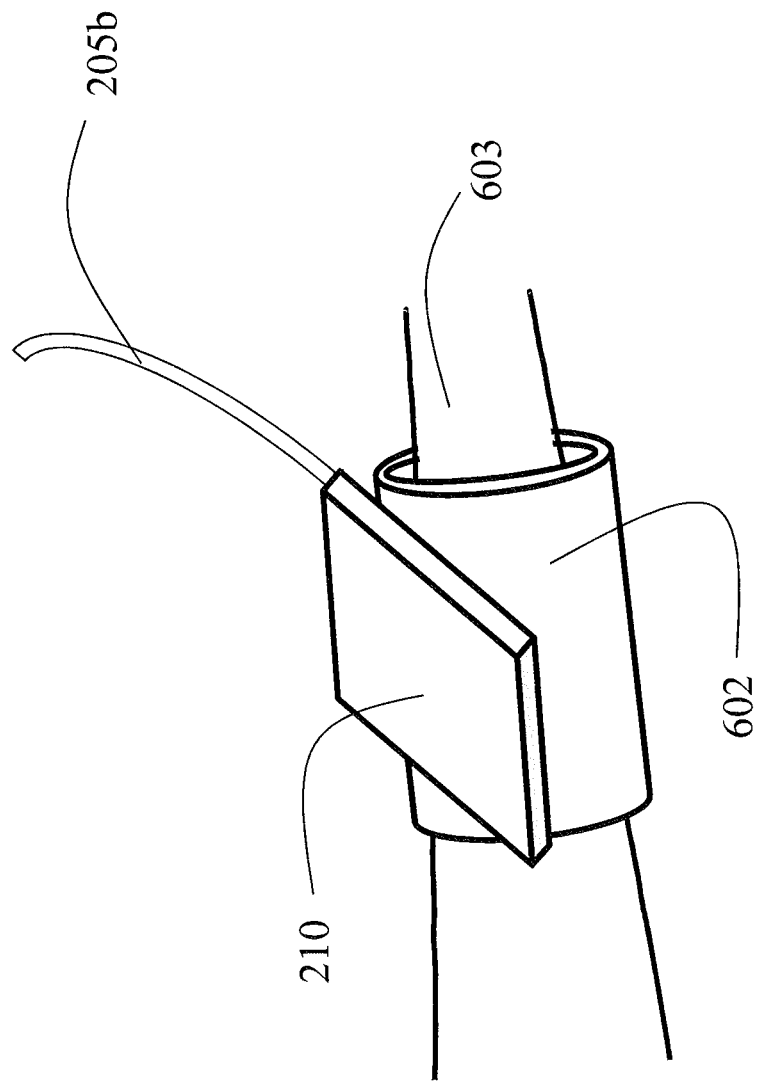
FIG. 6 illustrates an embodiment of an adjustable, quick mount mechanism for the portable display in FIGS. 2a to 5c, that can be employed to adjustably mount the portable display on a user's arm or wrist.

FIG. 6, illustrate "wearable" configurations of the portable control and display unit 210, where the portable control and display unit 210 is attached to the arm or wrist 603 of a user via a wearable attachment device. In more detail, a wide bracelet, wrist band or support structure 602, could be made of the soft Velcro material, where a strip of mating Velcro strip could be fixed behind the portable control and display unit 210 or its disposable cover. The Velcro arm band 602 can be employed for adjustable attachment or wearing of the portable control and display unit 210 on the arm or the wrist 603 of the user, as its' soft Velcro material grabs onto the back surface of the display and control unit 210 or its' secondary disposable sterile protective cover, that is equipped with mating Velcro.

The convenient and flexible Velcro based wearable attachment device of FIG. 6, can be adjusted using the adjustable Velcro mounting, to allow convenient direct viewing of the display 210 by the user during use, on the user's arm 603.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A laryngoscope device for insertion into an oral cavity, the device comprising:
    a disposable device body having an anatomical shape and including a proximal end and a distal end, the distal end being configured to be at least partially inserted into the oral cavity, the disposable device body including:
        a hollow passageway extending between the proximal and distal ends, the hollow passageway configured to be open at a proximal end opening located at the proximal end and a distal end opening located at the distal end, the proximal end opening and the distal end opening configured so that the hollow passageway is only open at the proximal end opening and the distal end opening; and
        an access channel adjacent to the hollow passageway, the access channel open at the proximal and distal ends and having an opening extending from the proximal end to the distal end along an entire length of the disposable device body, the opening of the access channel configured to provide a second device access to a trachea via the oral cavity in a manner that maintains the second device within the access channel until the second device exits the access channel at the distal end of the access channel;
    an opto-electronic module disposed at the distal end of the disposable device body and including an illumination source and one or more image sensors;
    electrical lines extending through the hollow passageway;
    an external power source, control electronics, and display device electrically coupled to the opto-electronic module via a flexible Universal Serial Bus (USB) cable configured to electrically connect each of the power source, control electronics, and display device to the electrical lines.

2. The device of claim 1, wherein the illumination source includes one or more of: a light emitting device (LED), a laser diode (LD), an ultraviolet (UV) light source, and an infrared (IR) light source, and wherein the image sensor includes one or more of: a CCD sensor, and a CMOS sensor.

3. The device of claim 2, wherein heat from the illumination source is directed to a window overlying the one or more image sensors for defogging purposes.

4. The device of claim 2, wherein the opto-electronic module is attached to one or more small flexible, rigid, or partially rigid, electronic boards within the disposable device body.

5. The device of claim 4, wherein the one or more electronic boards distribute power to the illumination source and the one or more image sensors at the distal end of the disposable device body, and serialize parallel digital imaging data or use MIPI output from the one or more image sensors and deliver the serial data through the electrical lines.

6. The device of claim 5, wherein the electrical lines continue to extend outside the disposable device body as a part of the USB cable to an end configured to connect directly to at least one of the display device and the control electronics.

7. The device of claim 6, wherein the control electronics are separate from the opto-electronic module and wherein a communication interface of the one or more electronic boards within the disposable device body to is a USB cable.

8. The device of claim 7, wherein the controller unit acts as a USB host, driving the one or more image sensors of the opto-electronic module as USB camera devices.

9. The device of claim 8, wherein the controller unit is configured to receive USB Video Class (UVC) video signals from the one or more electronic boards.

10. The device of claim 1, wherein the disposable device body is one or more of: rigid, partially rigid, flexible, partially flexible, and hollow inside and includes one or more of: a tool access hole and channel inside the device.

11. The device of claim 10, wherein other air tight tubing and channels run a length of the access channel inside the device to enable delivery of at least one of suction, air, liquid, and gel material to the distal end of the disposable device body.

12. The device of claim 1, wherein the disposable device body is an anatomically shaped laryngoscope with a metal blade and includes a lip in the metal blade and bumps or cutouts in the access channel to ease guiding of an endotracheal tube through the access channel into the body cavity.

13. The device of claim 1, further comprising spray nozzles at the distal end of the disposable device body and configured to spray lubricants on the endotracheal tube or other instruments as they pass or leave the access channel, deliver drugs to numb tissue adjacent the distal end, or to deliver chemicals to activate the tissue.

14. A device for insertion into a body cavity, the device comprising:
 a hollow tubular body having a proximal end and a distal end, the distal end being configured to be at least partially inserted into the body cavity, the hollow tubular body comprising:
  a hollow passageway extending between the proximal and distal ends, the hollow passageway configured to be open at a proximal end opening located at the proximal end and a distal end opening located at the distal end, the proximal end opening and the distal end opening configured so that the hollow passageway is only open at the proximal end opening and the distal end opening; and
  an access channel adjacent the hollow passageway and having an opening extending from the proximal end to the distal end along an entire length of the hollow tubular body, the opening of the access channel configured to provide a second device access to the body cavity in a manner that maintains the second device within the access channel until the second device exits the access channel;
 an opto-electronic module located at the distal end of the hollow tubular body and comprising an illumination source and at least one image sensor; and
 a control and display unit including a power source, control electronics, and image processing electronics electrically coupled to the opto-electronic module by flexible electrical lines extending through the hollow passageway from the proximal end to the distal end.

15. The device of claim 14, wherein the hollow tubular body comprises a flexible portion having an expandable accordion structure, and wherein a rigid, flexible, articulating or robotic medical body, can be inserted through the flexible tubular hollow portion.

16. The device of claim 15, wherein the expandable accordion structure enables the hollow tubular body to be moved between an expanded form and a collapsed form, the expanded form providing a shape retaining form before or during use of the device, and the collapsed form enabling elements to be pushed out of the hollow tubular body.

17. The device of claim 14, wherein the hollow tubular body of the device further comprises a separate imaging window interposed between the distal end of the hollow tubular body and the opto-electronic module, wherein heat from the illumination source or from a heat-generating resistor included in the device is directed to the imaging window to substantially prevent formation of condensation on the imaging window.

18. The device of claim 14, wherein the opto-electronic module is deployed and articulated out of an access channel within the hollow tubular body, the device having an insertion position in which the opto-electronic module is substantially contained within a profile of the hollow tubular body, and having an articulated position wherein at least a portion of the opto-electronic module is disposed external to the profile of the hollow tubular body.

19. The device of claim 14, further comprising a USB cable that electrically couples at least a portion of the flexible electrical lines to the control and display unit.

20. The device of claim 14, wherein the at least one image sensor comprises dual image sensors positioned at the distal tip, directed at a single field of vision, providing stereoscopic view of a site adjacent the dual image sensors.

21. The device of claim 14, wherein at least one of suction, irrigation, drug and diagnostic visualization agents are delivered to a site within the body cavity under observation, with built in air tight channels and tubes within the hollow tubular body of the device, and controlled by valves and other mechanical means at the proximal end or alternatively controlled electronically by the control electronics.

22. The device of claim 21, wherein output ports for at least one of suction, air, liquid and gel delivery are positioned adjacent at least one of the illumination source, the at least one image sensor, and an opening in an access channel at the distal end of the hollow tubular body.

23. The device of claim 21, wherein tubular extension for suction, air, liquid and gel delivery are provided at the proximal end of the device, and the tubular extension employs connection means to be attached to outside air, suction, liquid supply, disposable syringes, or pumps.

24. The device of claim 21, wherein certain air, or liquid valves are utilized at the proximal end to control, initiate, and continue process of suction, delivery, or spraying of material at the distal end.

25. The device of claim 19, wherein a small reservoir and containers are connected to a channel and tubing supply in the device, internal to a handle at the proximal end of the hollow tubular body or external to the handle.

26. The device of claim 25, wherein the small reservoir and containers are made void of air to be used for suction, or filled with medication or active agents to be delivered through the device.

27. A completely disposable anatomically-shaped laryngoscope, comprising:
 a body having a proximal end, a distal end, a hollow passageway extending between the proximal and distal ends, and an access channel configured to house an endotracheal tube, the access tube sharing a wall with the hollow passageway and having an opening extending from the proximal end to the distal end along a side opposite the shared wall, the hollow passageway configured to be open at a proximal end opening located at the proximal end and a distal end opening located at the distal end, the proximal end opening and the distal end opening configured so that the hollow passageway is only open at the proximal end opening and the distal end opening;

an optoelectronic module disposed in the hollow passageway of the body to leave the access channel free from obstructions; the optoelectronic module including:
  a component holding structure disposed over the hollow passageway at the distal end of the body;
  a vision module configured to capture image data, the vision module disposed in an opening in the component holding structure and coupled to an electronic circuit board positioned in the hollow passageway;
  an illumination module including at least one light source disposed in at least another opening in the component holding structure and coupled to flexible circuitry; and
  an electrical connection disposed within the hollow passageway and coupled on one end to the electronic circuit board and the flexible circuitry and coupled at an opposite end to a flexible cable that extends outwardly from the body.

28. The laryngoscope of claim 27, wherein the electrical connection is configured to receive at least one USB cable.

29. The laryngoscope of claim 27, wherein the body includes a substantially straight elongated portion and a curved portion at the distal end.

30. The laryngoscope of claim 27, further comprising at least one spray nozzle disposed over the access channel at the distal end of the body.

31. The laryngoscope of claim 27, wherein the illumination module is mounted adjacent a heat sink configured to direct heat generated by the at least one light source to a front surface of an imaging lens of the vision module.

32. The laryngoscope of claim 27, further comprising a rigid blade extending outwardly from a bottom portion of the distal end of the body.

33. The device of claim 14, wherein the at least one image sensor comprises a high resolution digital image sensor and the control electronics are configured to convert MIPI (Mobile Industry Processor Interface) output to USB Video Class (UVC) format.

34. The device of claim 14, wherein MIPI output from the at least one image sensor of the opto-electronic module is transmitted though flexible electrical lines extending through the hollow passageway from the proximal end to the distal end.

* * * * *

UNITED STATES PATENT AND TRADEMARK OFFICE
CERTIFICATE OF CORRECTION

PATENT NO. : 8,827,899 B2
APPLICATION NO. : 12/884363
DATED : September 9, 2014
INVENTOR(S) : Farr et al.

Page 1 of 1

It is certified that error appears in the above-identified patent and that said Letters Patent is hereby corrected as shown below:

On the Title Page, Item (75) Inventors should read:

--(75) Inventors: Ali Farr, Palo Alto, CA (US); Mina Farr, Palo Alto, CA (US); Chris Togami, San Jose, CA (US); Laleh Farr, Palo Alto, CA (US)--.

Signed and Sealed this
Twenty-third Day of June, 2015

Michelle K. Lee
*Director of the United States Patent and Trademark Office*